United States Patent
Chattopadhyay et al.

(10) Patent No.: US 10,851,051 B2
(45) Date of Patent: Dec. 1, 2020

(54) COMPOSITIONS AND METHODS FOR TREATING MULTIPLE MYELOMA

(71) Applicants: THE BROAD INSTITUTE, INC., Cambridge, MA (US); THE GENERAL HOSPITAL CORPORATION, Boston, MA (US); PRESIDENT AND FELLOWS OF HARVARD COLLEGE, Cambridge, MA (US)

(72) Inventors: Shrikanta Chattopadhyay, Boston, MA (US); Stuart L. Schreiber, Cambridge, MA (US); Zarko Boskovic, Cambridge, MA (US)

(73) Assignees: THE BROAD INSTITUTE, INC., Cambridge, MA (US); THE GENERAL HOSPITAL CORPORATION, Boston, MA (US); PRESIDENT AND FELLOWS OF HARVARD COLLEGE, Cambridge, MA (US)

(*) Notice: Subject to any disclaimer, the term of this patent is extended or adjusted under 35 U.S.C. 154(b) by 0 days.

(21) Appl. No.: 15/752,507

(22) PCT Filed: Aug. 12, 2016

(86) PCT No.: PCT/US2016/046856
§ 371 (c)(1),
(2) Date: Feb. 13, 2018

(87) PCT Pub. No.: WO2017/030987
PCT Pub. Date: Feb. 23, 2017

(65) Prior Publication Data
US 2019/0010120 A1    Jan. 10, 2019

Related U.S. Application Data

(60) Provisional application No. 62/205,382, filed on Aug. 14, 2015.

(51) Int. Cl.
*C07C 311/51* (2006.01)
*A61P 35/00* (2006.01)

(52) U.S. Cl.
CPC ............ *C07C 311/51* (2013.01); *A61P 35/00* (2018.01); *C07B 2200/05* (2013.01)

(58) Field of Classification Search
CPC ........................... C07D 311/51; C07C 311/51
See application file for complete search history.

(56) References Cited

U.S. PATENT DOCUMENTS

| | | | |
|---|---|---|---|
| 2011/0028509 A1* | 2/2011 | Crosignani | C07C 311/19 514/299 |
| 2011/0044991 A1 | 2/2011 | Dierks et al. | |
| 2011/0112075 A1 | 5/2011 | Follman et al. | |
| 2014/0314765 A1 | 10/2014 | Depinho et al. | |

OTHER PUBLICATIONS

CAS Registry No. 881289-59-4 (2006) (Year: 2006).*
CAS Registry No. 823822-73-7 (2005) (Year: 2005).*
CAS Registry No. 94870-40-3 (1985) (Year: 1985).*
CAS Abstract of Y. Osawa, Nippon Kagaku Zasski (1963) (Year: 1963).*
eMail Communication to CAS (Aug. 9, 2019) (Year: 2019).*
Y. Osawa, 84 Nippon Kagaku Zasski (1963) (Year: 1963).*
S. Chattopadhyay et al., 10 Cell Reports, 755-770 (2015) (Year: 2015).*
CAS Abstract and indexed Compounds A.P. Avdeenko et al., 45 Russian Journal of Organic Chemistry (2009) (Year: 2009).*
A.P. Avdeenko et al., 45 Russian Journal of Organic Chemistry (2009) (Year: 2009).*
CAS Abstract of RN 823822-75-9 (BRD9647) (2005) (Year: 2005).*
Chattopadhyay, S. et al., "Niche-Based Screening in Multiple Myeloma Identifies a Kinesin-5 Inhibitor with Improved Selectivity over Hematopoietic Progenitors," Feb. 10, 2015, Cell Reports; Issue 10, pp. 755-770; p. 757, paragraphs [2]-[4]; p. 758, figure 2C; p. 760, figure 3; p. 761, paragraph [1]; p. 762, figure 4; p. 763, paragraph [6]; p. 765, paragraph [1]; p. S2, paragraph [1].
Grado, VHL et al., Modulation of an ectodomain motif in the influenza A virus neuraminidase alters tetherin sensivity and results in virus attenuation in vivo; Mar. 20, 2014, Journal of Molecular Biology, vol. 426, Issue 6, pp. 1308-1321; p. 2, paragraph [2]; p. 8, paragraph [3].
International Search Report and Written

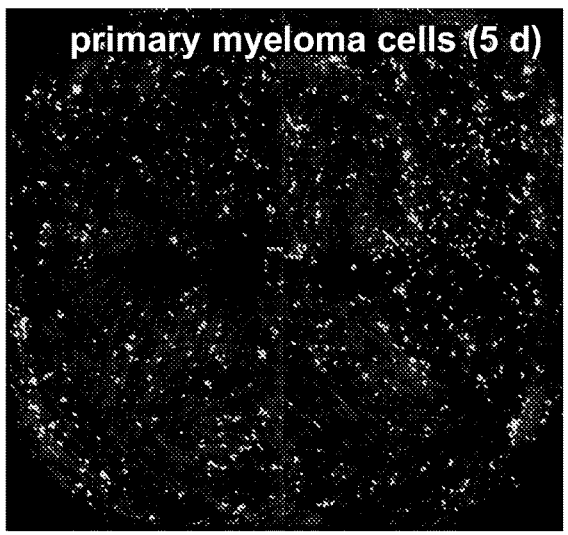 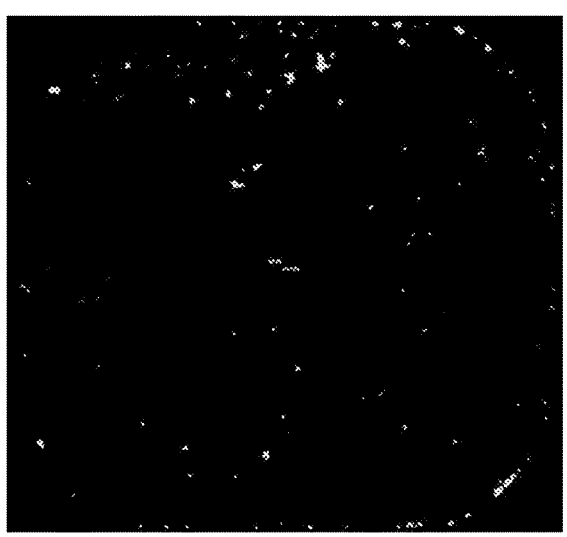
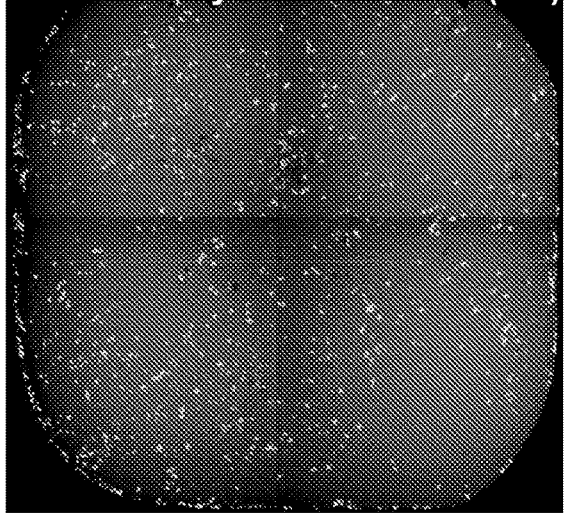 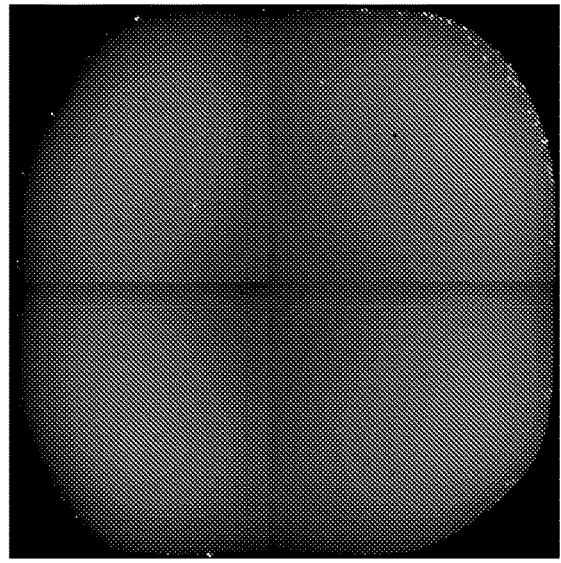
FIG. 1C

MOLP5 growth inhibition at 3d zb-179-3 zb-179-2 zb-16-14 zb-179-4

CMAP analysis

| by name | by name and cell line | by ATC code | | | | |
|---|---|---|---|---|---|---|
| rank | cmap name | mean | n | enrichment | p | specificity | % non-null |
| 1 | cephaeline | 0.845 | 5 | 0.999 | 0.00000 | 0.0000 | 100 |
| 2 | emetine | 0.837 | 4 | 0.999 | 0.00000 | 0.0000 | 100 |
| 3 | mitoxantrone | -0.670 | 3 | -0.998 | 0.00000 | 0.0000 | 100 |
| 4 | H-7 | -0.646 | 4 | -0.997 | 0.00000 | 0.0000 | 100 |
| 5 | anisomycin | 0.756 | 4 | 0.996 | 0.00000 | 0.0155 | 100 |
| 6 | puromycin | 0.581 | 4 | 0.987 | 0.00000 | 0.0112 | 100 |
| 7 | cicloheximide | 0.631 | 4 | 0.983 | 0.00000 | 0.0056 | 100 |
| 8 | ouabain | 0.573 | 4 | 0.971 | 0.00000 | 0.0050 | 100 |
| 9 | niclosamide | 0.436 | 5 | 0.942 | 0.00000 | 0.0052 | 100 |
| 10 | chlorcyclizine | 0.380 | 6 | 0.911 | 0.00000 | 0.0000 | 100 |

(Protein synthesis inhibitors in boxes)

FIG. 2C

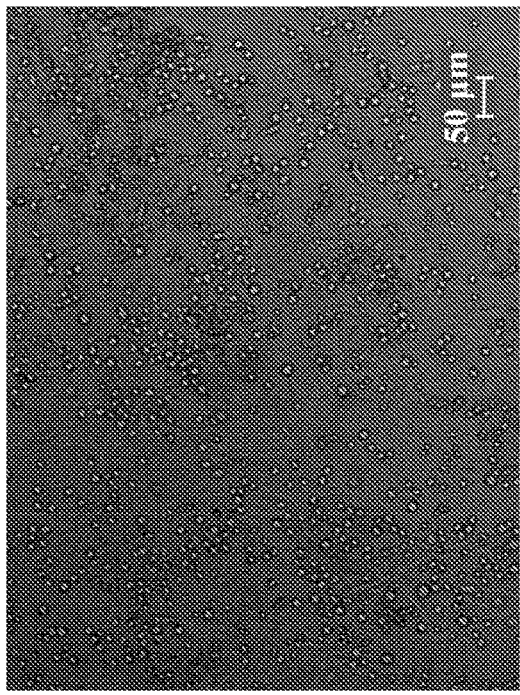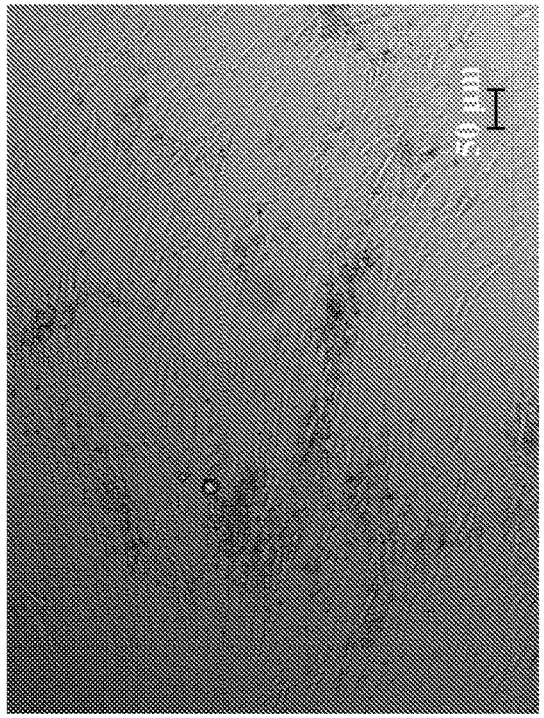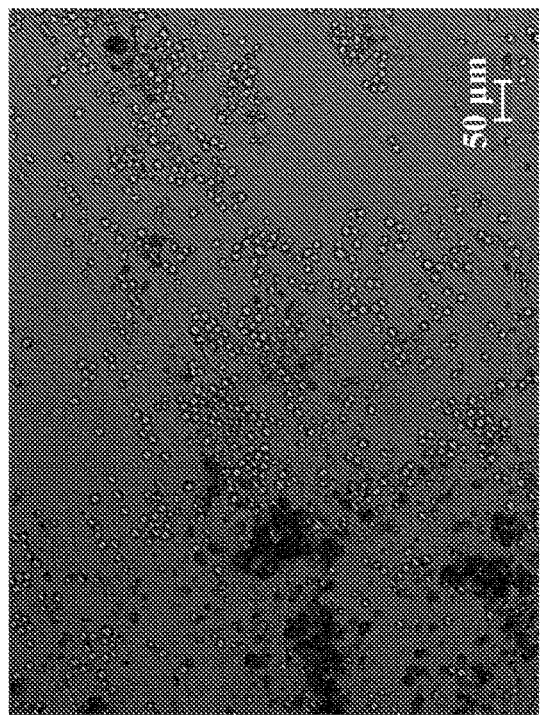
FIG. 4D (90% peak by LC-MS)

| Description | Score | Coverage | # Proteins | # Unique Peptides | # Peptides | # PSMs | Area | MW [kDa] | calc. pI |
|---|---|---|---|---|---|---|---|---|---|
| his4 H4[Homo sapiens], Genbank accession number: AAM83108, Z.Boskovic | 160.39 | 65.69 | 1 | 5 | 5 | 62 | 5.116E9 | 11.2 | 11.36 |

| A2 | Sequence | # PSMs | # Proteins | # Protein Groups | Protein Group Accesions | Modifications | ΔCn | Area | q-Value | PEP |
|---|---|---|---|---|---|---|---|---|---|---|
| High | RISGLIYEETRGVLK | 5 | 1 | 1 | 1zb | | 0.0000 | 5.601E9 | 0 | 0.0003323 |
| High | RQGRTLYGFGG | 1 | 1 | 1 | 1zb | | 0.0000 | 4.304E9 | 0 | 0.06348 |
| High | TVTAmDVVYALK | 1 | 1 | 1 | 1zb | M5(Oxidation); K12(Heavy Zarko) | 0.0000 | 9.393E6 | 0 | 0.1601 |
| High | TVTAmDVVYALK | 16 | 1 | 1 | 1zb | M5(Oxidation) | 0.0000 | 3.060E9 | 0 | 0.002521 |
| High | TVTAMDVVYALK | 34 | 1 | 1 | 1zb | | 0.0000 | 5.444E9 | 0 | 0.001207 |
| High | VFLEnVIRDAVTYTEHAK | 1 | 1 | 1 | 1zb | N5(Deamidated) | 0.0000 | 0.000E0 | 0 | 0.228 |
| High | VFLENVIRDAVTYTEHAK | 2 | 1 | 1 | 1zb | | 0.0000 | 1.048E7 | 0 | 0.04873 |
| High | VLRDNIQGITK | 2 | 1 | 1 | 1zb | | 0.0000 | 5.859E8 | 0 | 0.05301 |

| Description | Score | Coverage | # Proteins | # Unique Peptides | # Peptides | # PSMs | # AAs | MW [kDa] | calc. pI |
|---|---|---|---|---|---|---|---|---|---|
| his4 H4[Homo sapiens], Genbank accession number: AAM83108, Z.Boskovic | 181.30 | 65.69 | 1 | 5 | 5 | 64 | 102 | 11.2 | 11.36 |

| A2 | Sequence | # PSMs | # Protein Groups | # Proteins | Protein Group Accesions | Modifications | ΔCn | Area | q-Value | PEP |
|---|---|---|---|---|---|---|---|---|---|---|
| High | VFLENVIRDAVTYTEHAK | 3 | 1 | 1 | zb | | 0.0000 | 4.017E7 | 0 | 0.02289 |
| High | VFLEnVIRDAVTYTEHAK | 1 | 1 | 1 | zb | N5(Deamidated) | 0.0000 | 2.825E6 | 0 | 0.000729 |
| High | TVTAMDVVYALK | 35 | 1 | 1 | zb | | 0.0000 | 4.666E9 | 0 | 0.04196 |
| High | RISGLIYEETRGVLK | 11 | 1 | 1 | zb | | 0.0000 | 7.179E9 | 0 | 0.003876 |
| High | TVTAmDVVYALK | 10 | 1 | 1 | zb | M5(Oxidation) | 0.0000 | 3.291E9 | 0 | 0.01217 |
| High | VLRDNIQGITK | 2 | 1 | 1 | zb | | 0.0000 | 6.140E8 | 0 | 0.09296 |
| High | TVTAMDVYALk | 1 | 1 | 1 | zb | K12(Heavy Zarko) | 0.0000 | 0.000E0 | 0 | 0.04048 |
| High | RqGRTLYGFGG | 1 | 1 | 1 | zb | Q2(Deamidated) | 0.0000 | 2.655E7 | 0 | 0.1447 |

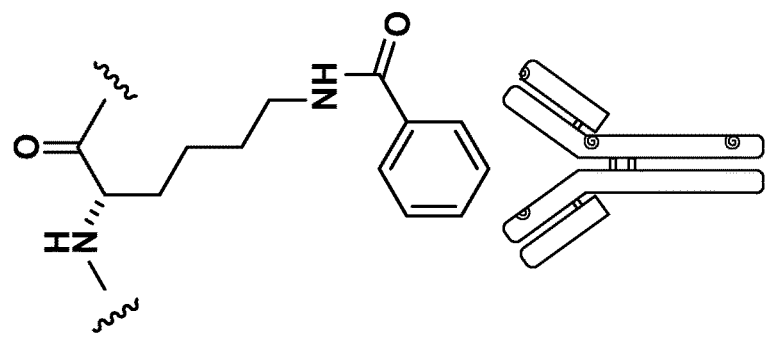
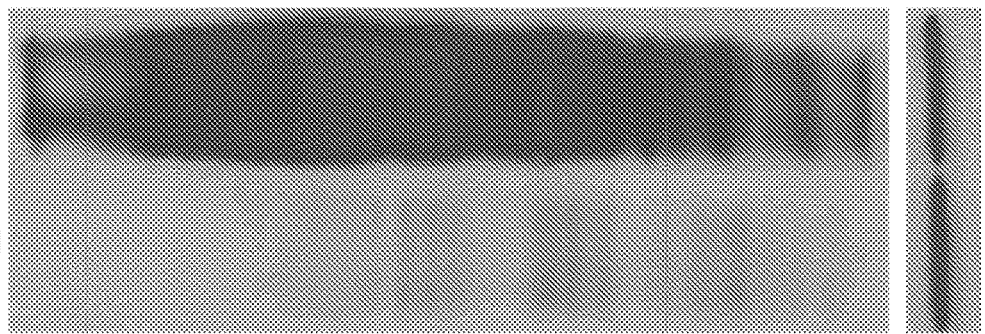
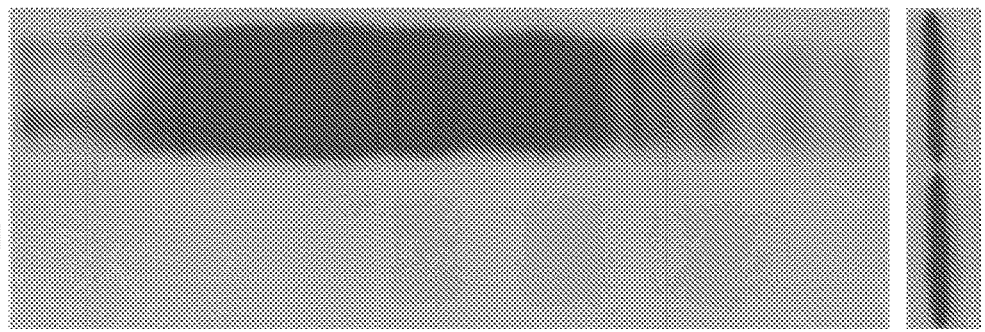
FIG. 15

COMPOSITIONS AND METHODS FOR TREATING MULTIPLE MYELOMA

CROSS-REFERENCE TO RELATED APPLICATION

This application is the U.S. national phase application, pursuant to 35 U.S.C. § 371, of PCT International application Serial No.: PCT/US2016/046856, filed Aug. 12, 2016, designating the United States and published in English, which claims the benefit of the following U.S. Provisional Application No.: 62/205,382, filed Aug. 14, 2015, the entire contents of each of which are incorporated herein by reference.

STATEMENT OF RIGHTS TO INVENTIONS MADE UNDER FEDERALLY SPONSORED RESEARCH

This invention was made with Government support under Grant Nos. 2R01-GM038627 and 5K08CA158149 awarded by the National Institutes of Health. The Government has certain rights in the invention.

BACKGROUND OF THE INVENTION

Cancer continues to be a major global health burden. Despite progress in the treatment of cancer, there continues to be an unmet medical need for more effective and less toxic therapies, especially for those patients with advanced disease or cancers that are resistant to existing therapeutics. For example, multiple myeloma is a malignant plasma cell disorder and is the second most common hematologic malignancy in the United States, with about 20 000 patients diagnosed annually. Most patients diagnosed with multiple myeloma survive for only 2-3 years. However, for most multiple myeloma patients, the disease eventually progresses or returns, and over time treatment resistance often develops. New less-toxic methods and therapeutics that have better therapeutic efficacy, particularly for patients with multiple myeloma, are urgently required. In addition, new methods for probing cancer cells to discover cellular mechanisms to inform potential therapeutic strategies are urgently required.

SUMMARY OF THE INVENTION

As described below, the present invention features compositions and methods for inhibiting proliferation of a multiple myeloma cell.

The invention also provides derivatives or analogs of BRD9647 that are able to inhibit the proliferation of multiple myeloma cells. These compounds may have the structure of formula (I):

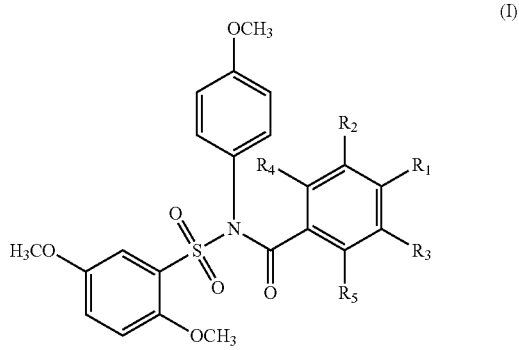

wherein $R_1$-$R_5$ are independently selected from hydrogen, —F; —Cl; —Br; —I; —OH; —R*; —OR*; —NH$_2$; —NHR*; —N(R*)$_2$; —N(R*)$_3$+; —N(R*)—OH; —N(→*O)(R*)$_2$; —O—N(R*)$_2$; —N(R*)—O—R*; —N(R*)—N(R*)$_2$; —C=N—R*; —N=C(R*)$_2$; —C=N—N(R*)$_2$; —C(=NR*)(—N(R*)$_2$); —C(H)(=N—OH); —SH; —SR*; —CN; —NC; —C(=O)—R*; —CHO; —CO$_2$H; —CO$_2$—; —CO$_2$R*; —C(=O)—S—R*; —O—(C=O)—H; —O—(C=O)—R*; —S—C(=O)—R*; —(C=O)—NH$_2$; —C(=O)—N(R*)$_2$; —C(=O)—NHNH$_2$; —O—C(=O)—NHNH$_2$; —C(=S)—NH$_2$; —(C=S)—N(R*)$_2$; —N(R*)—CHO; —N(R*)—C(=O)—R*; —C(=NR*)—O—R*; —O—C(=NR*)—R*; —SCN; —NCS; —NSO; —SSR*; —N(R*)—C(=O)—N(R*)$_2$; —N(R*)—C(=S)—N(R*)$_2$; —S(=O)$_{1-2}$—R*; —O—S(=O)$_2$—R*; —S(=O)$_2$—OR*; —N(R*)—S(=O)$_2$—R*; —S(=O)$_2$—N(R*)$_2$; —O—SO$_3$; —O—S(=O)$_2$—OR*; —O—S(=O)—OR*; —O—S(=O)—R*; —S(=O)—OR*; —S(=O)—R*; —NO; —NO$_2$; —NO$_3$; —O—NO; —O—NO$_2$; —N$_3$; —N$_2$—R*; —N(C$_2$H$_4$); —Si(R*)$_3$; —CF$_3$; —O—CF$_3$; —O—CH$_3$; —O—(CH$_2$)$_{1-6}$CH$_3$; —PR*$_2$; —O—P(=O)(OR*)$_2$; and —P(=O)(OR*)$_2$;

R* is, independently at each occurrence from hydrogen, and a $C_{1-10}$ (e.g., $C_{1-8}$ or $C_{1-6}$ or $C_{1-4}$ or $C_{1-2}$) hydrocarbon (e.g., alkyl, alkenyl, alkynyl, aryl (e.g., phenyl), alkyl-aryl (e.g., benzyl), aryl-alkyl (e.g., toluyl), etc.); where at least one of $R_1$-$R_5$ is not hydrogen;

or pharmaceutically acceptable salts thereof. When R* is a hydrocarbon, it to be understood that R* is the monovalent radical of a hydrocarbon bonded at the specified position. For example, if R* is a $C_1$ hydrocarbon, R* is —CH$_3$ (i.e., methyl). In some embodiments $R_1$-$R_5$ are independently selected from hydrogen, —OH, —SH, —NH$_2$; —N(R*)$_2$; —R*; —OR*; —F; —Cl; and/or —Br. In some embodiments, $R_1$ is fluorine, chlorine, bromine, or iodine. In some embodiments, $R_2$-$R_5$ are each hydrogen. In some embodiments, $R_1$ is fluorine. In some embodiments, $R_2$ and/or $R_3$ are independently fluorine, chlorine, bromine or iodine. In some embodiments, $R_2$ and/or $R_3$ are fluorine. In some embodiments, $R_4$ and/or $R_5$ are independently fluorine, chlorine, bromine or iodine. In some embodiments, $R_4$ and/or $R_5$ are fluorine. In some embodiments, at least two (e.g. three, four, etc.) of $R_1$-$R_5$ are independently fluorine, chlorine, bromine or iodine.

In other embodiments, the derivatives or analogs of BRD9647 have the structure of formula (II):

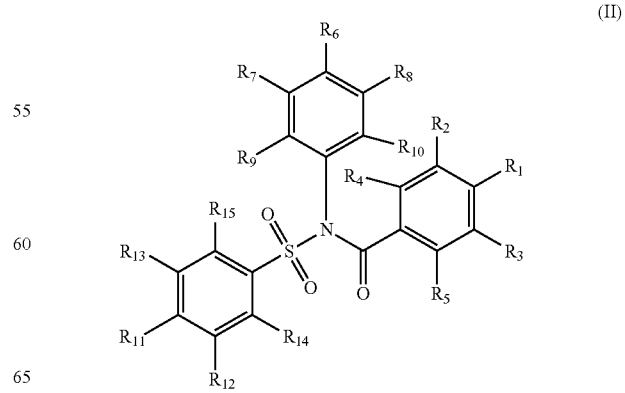

wherein $R_1$-$R_{15}$ are each independently selected from hydrogen, —F; —Cl; —Br; —I; —R*; —OH; —OR*; —$NH_2$; —NHR*; —N(R*)$_2$; —N(R*)$_3^+$; —N(R*)—OH; —N(→O)(R*)$_2$; —O—N(R*)$_2$; —N(R*)—O—R*; —N(R*)—N(R*)$_2$; —C=N—R*; —N=C(R*)$_2$; —C=N—N(R*)$_2$; —C(=NR*)(—N(R*)$_2$); —C(H)(=N—OH); —SH; —SR*; —CN; —NC; —C(=O)—R*; —CHO; —$CO_2$H; —$CO_2$—; —$CO_2$R*; —C(=O)—S—R*; —O—(C=O)—H; —O—(C=O)—R*; —S—C(=O)—R*; —(C=O)—$NH_2$; —C(=O)—N(R*)$_2$; —C(=O)—$NHNH_2$; —O—C(=O)—$NHNH_2$; —C(=S)—$NH_2$; —(C=S)—N(R*)$_2$; —N(R*)—CHO; —N(R*)—C(=O)—R*; —C(=NR*)—O—R*; —O—C(=NR*)—R*; —SCN; —NCS; —NSO; —SSR*; —N(R*)—C(=O)—N(R*)$_2$; —N(R*)—C(=S)—N(R*)$_2$; —S(=O)$_{1-2}$—R*; —O—S(=O)$_2$—R*; —S(=O)$_2$—OR*; —N(R*)—S(=O)$_2$—R*; —S(=O)$_2$—N(R*)$_2$; —O—$SO_3$; —O—S(=O)$_2$—OR*; —O—S(=O)—OR*; —O—S(=O)—R*; —S(=O)—OR*; —S(=O)—R*; —NO; —$NO_2$; —$NO_3$; —O—NO; —O—$NO_2$; —$N_3$; —$N_2$—R*; —N($C_2H_4$); —Si(R*)$_3$; —$CF_3$; —O—$CF_3$; —O—$CH_3$; —O—($CH_2$)$_{1-6}CH_3$; —PR*$_2$; —O—P(=O)(OR*)$_2$; and —P(=O)(OR*)$_2$;

R* is, independently at each occurrence from hydrogen, and a $C_{1-10}$ (e.g., $C_{1-8}$ or $C_{1-6}$ or $C_{1-4}$) hydrocarbon (e.g., alkyl, alkenyl, alkynyl, aryl (e.g., phenyl), alkyl-aryl (e.g., benzyl), aryl-alkyl (e.g., toluyl), etc.). In some embodiments, the compound is not BRD9647. In some embodiments $R_1$-$R_{15}$ are independently selected from the group consisting of hydrogen, —OH, —SH, —$NH_2$; —N(R*)$_2$; —R*; —OR*; —F; —Cl; and/or —Br. In some embodiments, $R_1$-$R_5$ are each hydrogen. In some embodiments, $R_1$-$R_{15}$ may be methoxy, ethoxy or propoxy. In some embodiments, $R_6$ is methoxy, ethoxy, or propoxy. In some embodiments, at least one of $R_{11}$-$R_{15}$ is not hydrogen. In some embodiments, $R_{11}$-$R_{15}$ are independently selected from hydrogen, methoxy, fluorine or bromine.

In some aspects, the compound is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this invention.

Geometric isomers can be represented by the symbol ----- which denotes a bond that can be a single, double or triple bond as described herein. Provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

The term "enantiomers" refers to a pair of stereoisomers that are non-superimposable mirror images of each other. An atom having an asymmetric set of substituents can give rise to an enantiomer. A mixture of a pair of enantiomers in any proportion can be known as a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)—. The present chemical entities, pharmaceutical compositions and methods are meant to include all such possible isomers, including racemic mixtures, optically substantially pure forms and intermediate mixtures.

Optically active (R)- and (S)-isomers can be prepared, for example, using chiral synthons or chiral reagents, or resolved using conventional techniques. Enantiomers can be isolated from racemic mixtures by any method known to those skilled in the art, including chiral high pressure liquid chromatography (HPLC), the formation and crystallization of chiral salts, or prepared by asymmetric syntheses.

Optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid. The separation of the mixture of diastereoisomers by crystallization followed by liberation of the optically active bases from these salts affords separation of the isomers. Another method involves synthesis of covalent diastereoisomeric molecules by reacting disclosed compounds with an optically pure acid in an activated form or an optically pure isocyanate. The synthesized diastereoisomers can be separated by conventional means such as chromatography, distillation, crystallization or sublimation, and then hydrolyzed to deliver the enantiomerically enriched compound. Optically active compounds can also be obtained by using active starting materials. In some embodiments, these isomers can be in the form of a free acid, a free base, an ester or a salt.

In certain embodiments, the compound of the invention can be a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to- (a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

All chiral, diastereomeric, racemic, and geometric isomeric forms of a structure are intended, unless specific stereochemistry or isomeric form is specifically indicated. All processes used to prepare compounds of the present invention and intermediates made therein are considered to be part of the present invention. All tautomers of shown or described compounds are also considered to be part of the present invention.

In another aspect, the invention provides a method of inhibiting proliferation of a cancer cell, the method comprising covalently modifying a residue of a polypeptide in the cell, wherein the modification is addition or removal of a benzoyl group. In some embodiments, the modification is the addition or removal of a benzoyl derivative having the structure:

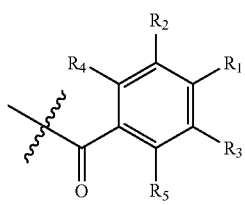

wherein $R_1$-$R_5$ are each independently selected from hydrogen, —F; —Cl; —Br; —I; —OH; —R*; —OR*; —NH$_2$; —NHR*; —N(R*)$_2$; —N(R*)$_3^+$; —N(R*)—OH; —N(→O)(R*)$_2$; —O—N(R*)$_2$; —N(R*)—O—R*; —N(R*)—N(R*)$_2$; —C≡N—R*; —N═C(R*)$_2$; —C═N—N(R*)$_2$; —C(═NR*)(—N(R*)$_2$); —C(H)(═N—OH); —SH; —SR*; —CN; —NC; —C(═O)—R*; —CHO; —CO$_2$H; —CO$_2^-$; —CO$_2$R*; —C(═O)—S—R*; —O—(C═O)—H; —O—(C═O)—R*; —S—C(═O)—R*; —(C═O)—NH$_2$; —C(═O)—N(R*)$_2$; —C(═O)—NHNH$_2$; —O—C(═O)—NHNH$_2$; —C(═S)—NH$_2$; —(C═S)—N(R*)$_2$; —N(R*)—CHO; —N(R*)—C(═O)—R*; —C(═NR*)—O—R*; —O—C(═NR*)—R*; —SCN; —NCS; —NSO; —SSR*; —N(R*)—C(═O)—N(R*)$_2$; —N(R*)—C(═S)—N(R*)$_2$; —S(═O)$_{1-2}$—R*; —O—S(═O)$_2$—R*; —S(═O)$_2$—OR*; —N(R*)—S(═O)$_2$—R*; —S(═O)$_2$—N(R*)$_2$; —O—SO$_3$; —O—S(═O)$_2$—OR*; —O—S(═O)—OR*; —O—S(═O)—R*; —S(═O)—OR*; —S(═O)—R*; —NO; —NO$_2$; —NO$_3$; —O—NO; —O—NO$_2$; —N$_3$; —N$_2$—R*; —N(C$_2$H$_4$); —Si(R*)$_3$; —CF$_3$; —O—CF$_3$; —O—CH$_3$; —O—(CH$_2$)$_{1-6}$CH$_3$; —PR*$_2$; —O—P(═O)(OR*)$_2$; and —P(═O)(OR*)$_2$;

R* is, independently at each occurrence from hydrogen, and a C$_{1-10}$ (e.g., C$_{1-8}$ or C$_{1-6}$ or C$_{1-4}$) hydrocarbon (e.g., alkyl, alkenyl, alkynyl, aryl (e.g., phenyl), alkyl-aryl (e.g., benzyl), aryl-alkyl (e.g., toluyl), etc.). In some embodiments $R_1$-$R_5$ are independently selected from —OH, —SH, —NH$_2$; —N(R*)$_2$; —OR*; —F; —Cl; and/or —Br.

In various embodiments, the cancer cell is a stroma-dependent multiple myeloma cell. In other embodiments, the cell comprises a AZIN1 polynucleotide or polypeptide having a mutation. In still other embodiments, the polypeptide in the cell is modified by contacting the cell with BRD9647. In various embodiments, the modification is addition of a benzoyl group.

In another aspect, the invention provides a pharmaceutical composition comprising an effective amount of BRD9647 in a pharmaceutically acceptable carrier. In yet another aspect, the invention provides a method of treating multiple myeloma in a subject, the method comprising administering to the subject the pharmaceutical composition according to any aspect delineated herein. In still another aspect, the invention provides a kit comprising a pharmaceutical composition according to any aspect delineated herein. In various embodiments, the kit further comprises a capture reagent detecting a AZIN1 polynucleotide or polypeptide.

In another aspect, the invention provides a composition comprising a BRD9647 having a detectable label. In various embodiments of any aspect delineated herein, the detectable label is on a benzoyl group of BRD9647 or a derivative thereof. In various embodiments of any aspect delineated herein, the detectable label is an isotopic label. In various embodiments of any aspect delineated herein, the isotopic label is $^{13}$C, $^{14}$C, or D$_5$. In some embodiments, the detectable label is on the benzoyl group of any compound of Formula I or II.

In yet another aspect, the invention provides a kit comprising a composition according to any aspect delineated herein.

In another aspect, the invention provides a method of modulating benzoylation of an agent in a cell, the method comprising contacting the cell with BRD9647 or a derivative thereof or the composition according to any aspect delineated herein, thereby modulating benzoylation of an agent in the cell. In still another aspect, the invention provides a method of characterizing benzoylation of an agent in a cell, the method comprising contacting the cell with a composition according to any aspect delineated herein and measuring benzoylation of the agent by detecting a detectable label on the agent. In some embodiments, the derivative thereof is any compound of Formula I or II.

In another aspect, the invention provides a method of identifying an agent in a cell that is a substrate for benzoylation, the method comprising contacting the cell with BRD9647 or a derivative thereof or a composition according to any aspect delineated herein and measuring benzoylation of the agent relative to a reference, wherein an alteration in benzoylation indicates that the agent is a substrate for benzoylation. In some embodiments, the derivative thereof is any compound of Formula I or II.

In various embodiments of any aspect delineated herein, the cell is a cancer cell. In various embodiments, the cell is a multiple myeloma cell. In other embodiments, the agent is a polypeptide. In still other embodiments, the benzoylation of the agent is measured by immunoassay, mass spectrometry, or autoradiography. In various embodiments, the detectable label is an isotopic label. In other embodiments, the isotopic label is detected by mass spectrometry or autoradiography.

Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid. An analog of BRD9647, for example, includes one or more substitutions of hydrogen with a halogen. An analog of BRD9647 may be halogen functionalized at any carbon of the aromatic ring in the benzoyl group of BRD9647. In some embodiments, analogs of BRD9647 are fluorine functionalized in the benzoyl group.

By "AZIN1 polypeptide" is meant a polypeptide or fragment thereof having at least about 85% or greater amino acid identity to the amino acid sequence provided at NCBI Accession No. NP_680479 or NP_001288597 (various isoforms) and having antizyme binding or inhibiting activity. The AZIN1 polypeptide sequence at NCBI Accession No. NP_680479 is provided below:

```
  1 mkgfiddany svglldegtn lgnvidnyvy ehtltgknaf fvgdlgkivk khsqwqnvva 61 qikpfytvkc nsapavleil aalgtgfacs sknemalvqe lgvppeniiy ispckqvsqi 121 kyaakvgvni ltcdneielk kiarnhpnak vllhiatedn iggeegnmkf gttlkncrhl 181 lecakeldvq iigvkfhvss ackesqvyvh alsdarcvfd mageigftmn mldigggftg 241 tefqleevnh visplldiyf pegsgvkiis epgsyyvssa ftlavniiak kvvendkfps 301 gvektgsdep afmyymndgv ygsfasklse dlntipevhk kykedeplft sslwgpscde 361 ldqivescll pelnvgdwli fdnmgadsfh epsafndfqr paiyymmsfs dwyemqdagi 421 tsdsmmknff fvpsciqlsq edsfsaea
```

In one embodiment, an AZIN1 polypeptide comprises a mutation that confers BRD9647 sensitivity, or that alters (increases/decreases) antizyme inhibitory activity. In one particular embodiment, an AZIN1 polypeptide comprises an S367G mutation.

By "AZIN1 polynucleotide" is meant a polynucleotide encoding a AZIN1 polypeptide. An exemplary AZIN1 polynucleotide sequence is provided at NCBI Accession No. NM_148174. The sequence is provided below:

```
  1 ctaatataaa tactggcgtc gctggcgccg ccttctcaca ctttcaggct ctgatcgcgg 61 ccgcagtttt tccttttttc ttctgccgtc gccttctctg cctcttctca tcctttctcg 121 ctctgctgct ctgcagtgtg acgagtccga atcctcttcc cacccagccc gcgcctttct 181 tcttttgcct gcgctgttct atttctcctt cggccgccgc cgccactgct gcacacagct 241 ggtgtcggtg ccgcgctttt accccaagt cgttcccgca gcctatggcc caggccgcct 301 tgggtatttc tgctcaaggt aaccacatcc ctctttaaaa attccgccga aaaagagaag 361 acgcttacc cgactctttg ggccgttatc tcacggcgaa cttctgacc aagtatacaa 421 ctacccagag ggcctaggag aagtgctgta tagagagcag ttcgacttca acgctgagcc
```

-continued

```
 481 accttgggaa cctagctgat gatagggggg ttccatctcc caacttgtcc attttgttgc 541 atattctaag gacccagaca taggcttggt ggcccgtctc ttgtcttccc tggtttatga 601 ctttcggctt tgtggaatac ggctgagatg aaaggattta ttgatgatgc aaactactcc 661 gttggcctgt tggatgaagg aacaaacctt ggaaatgtta ttgataacta tgtttatgaa 721 catacccctga cagggaaaaa tgcatttttt gtgggagatc ttggaaagat tgtgaagaaa 781 cacagtcaat ggcagaatgt agtggctcag ataaagccat tctacacagt gaagtgcaac 841 tctgctccag ctgtacttga gattttggca gctcttggaa ccggatttgc ttgttccagt 901 aaaaatgaaa tggctttagt gcaagagttg ggtgtacctc cagaaaacat tatttacata 961 agtccttgca agcaagtgtc tcagataaag tatgcagcaa agttggagt gaatatcctg 1021 acatgtgaca atgaaattga attgaagaaa attgcacgta atcacccaaa tgccaaggtc 1081 ttactacata ttgcaacaga agataatatt ggaggtgaag agggtaacat gaagtttggc 1141 actaccctga agaactgtag gcatctcttg gaatgtgcta aggaacttga tgtccaaata 1201 attggggtta aatttcatgt ttcgagtgct tgcaaagaat ctcaagtata tgtacatgct 1261 ctatctgatg ctcgatgtgt gtttgacatg gctggagaaa ttggctttac gatgaacatg 1321 ttagacattg gtggaggatt cacgggaact gaatttcaat tggaagaggt taatcatgtt 1381 atcagccctc tgttggatat ctactttcct gaaggatctg gtgttaagat aatttcagaa 1441 cccggaagct actatgtgtc ttctgcattt acactcgcag ttaatatcat agcaaagaaa 1501 gttgttgaaa atgataaatt tccctctgga gtagaaaaaa ccggaagtga tgaaccagcc 1561 ttcatgtatt atatgaatga tggtgtttat ggttcttttg caagtaaact gtctgaggac 1621 ttaaatacca ttccagaggt tcacaagaaa tacaaggaag atgagcctct gtttacaagc 1681 agcctttggg gtccatcctg tgatgagctt gatcaaattg tggaaagctg tcttcttcct 1741 gagctgaatg tgggagattg gcttatcttt gataacatgg gagcagattc tttccatgaa 1801 ccatctgctt ttaatgattt tcagaggcca gccatttatt acatgatgtc attcagtgat 1861 tggtatgaga tgcaagatgc tggaattact tcagactcaa tgatgaagaa cttcttcttt 1921 gtgccttctt gcattcagct gagccaagaa gacagctttt ccgctgaagc ttaaacaggc 1981 attaacgctt ctttagatct gaagttgcag gttaagcttg tctggtcaac attccagtgt 2041 ggaaaaataa tttaaacaat cttattctct taattctttt ggcaacaaaa actattagta 2101 atagctattt gggaccagac aaaatcagct ttcatctata attcattggg gataatggga 2161 gatttagata atgtatccag atttaaacct accagtttgt cctacccctt aagcgtttaa 2221 aataaaatat gcaacaaaat ggatgactta gtggagatgg aagcccatta attgggttcc 2281 ccattaaatc gttacatac aagaacacag ttttatact aaggatttgt gtttaaagtc 2341 ttgtaaagtt catgtctttc acccagatat atcaaatgtt agaagaccag tgtgacttca 2401 ttagataacg tttagtgtat ttagaatgtg taaatttgtg ctttgaactg tagtttaata 2461 aatgtaaaat tgcatcatag tatttgttga cctaatgtaa cccttgtatg attgcaataa 2521 aattttgtgt agattttact gttttttcag gctaaaactt tgggaaggg gctagctagc 2581 aaaggtagtt ttgaaataga tgtgtatatg gactgttttg aagggttttt ttctttatag 2641 cccagttaag ttttgtttgg ctcggtgcat ttttcattta tttaattagt aatttaagta
```

-continued

```
2701 aagtgtttgg taaatcattg tgaagttcag attcattatg gagagttgat gtgcagtaag
2761 catgatgttt aacaatttta acaccaaaaa tgttaatcct gcataaatca actgtaataa
2821 taaataggtg tttctgtata gatagaatgc atagagtacc ttagtaaatc tttgaatcac
2881 aatcttttgg ctgaaatgga agattctgtt aaatactttg aataaacttg ggggagggga
2941 aataaaattg cagaaaactg cagagcacta aaacttaaag aagggctaca tctttatcca
3001 gaaacctgtt gctcttttgc acggaatgtt taaattcaga gttgggatgg gggttggggt
3061 gaagcacact tattatcttc agttgcagtg atttcaaatt taggattttt tgttgttggt
3121 ttgaactgtc cccttagttt cttgttattt ccaatttgtt ctgcttagtc attacttttta
3181 attcttttct tactaaaatt ttatggtggt tgggggaagg gagttagcat cactaacctg
3241 acagttgttg ccaggaattt gctttgttta ctgctagtat attagaaatc ctagatctca
3301 gaatcacaat agtaataaac aacagggtc atttttcct aacttactct gtgttcaggt
3361 gtggaatttc tgtctcccaa gaggaaatgt gacttcactt tggtgccaat ggacagaaaa
3421 ttctacctgt gctacatagg agaagtttgg aatgcactta atagctggtt tttacacctt
3481 gatttcgagg tggaaagaaa ttgatcatga atctctaata aatttaaatc tcttaaacca
3541 gtaggtgctt aatattttt gatttgatta atgcccattt aaatctcatg ggttctatta
3601 aaaatatata tatatagggc cccaatccat tgccatcaaa ttgcccttgg acttttccaa
3661 ggtatattat ggggttttat gcaaaattcc aagctaccat gtaacttttt ttaaccattt
3721 aacaaggagg gggaactgtt tcctaccttc tttacatgtt gtgcattgtt gtggtccaga
3781 aatgccaaac cttttttaaag atggtgcaac tttgagtcct tggcttgact atacaggcct
3841 tgaacttcat ggcatatcaa ctttgccata tctgcaggag agctgttcta taagaaatag
3901 ctcagagttg caaatatcac atgtgaatga tacggtaact tttaagaaat gtctgtattg
3961 tatttgaaga ctgtttgcca taaatctgaa atttgaacct atgtatttca atttggtatg
4021 ctaaaaagtt ctgaattaat gtaaagtttt ttgttataat attgtaatct cagttcaaaa
4081 gttaactgca aatataaaac ccaatgattt ctatatagta aattgaactg taaaggtaac
4141 ttgtgtgtga ttctgaatac atagataaat gtttttattc ctcatgtttt actttggctt
4201 ctatctgaaa tagaggtaaa attttacata tcagcttta
```

By "BRD9647" is meant a compound having the formula shown below:

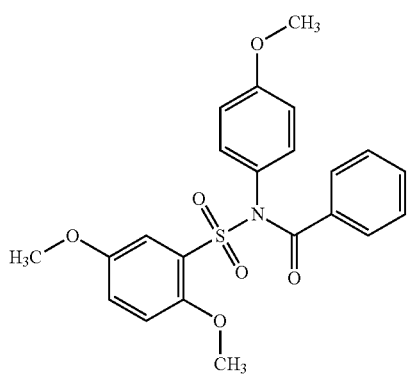 [SMILES: COc1ccc(N(C(=O)c2ccccc2)S(=O)(=O)c2cc(OC)ccc2OC)cc1]

By "Compound 1" or "zb-179-3" is meant a compound having the formula shown below:

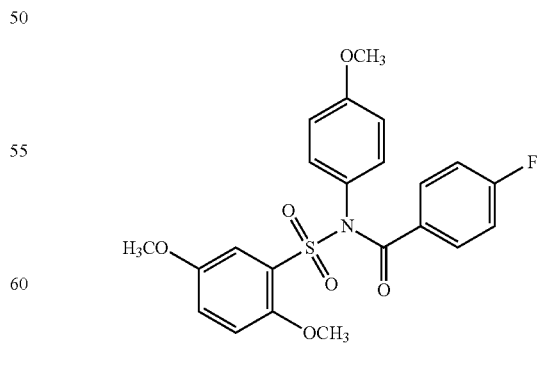

By "Compound 2" or "zb-179-2" is meant a compound having the formula shown below:

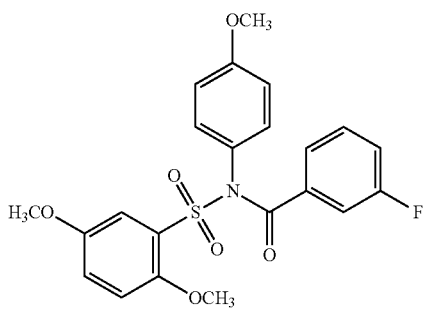 [SMILES: COc1ccc(N(C(=O)c2cccc(F)c2)S(=O)(=O)c2cc(OC)ccc2OC)cc1]

By "Compound 3" or "zb-16-14" is meant a compound having the formula shown below:

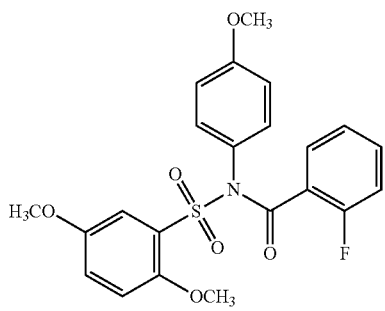 [SMILES: COc1ccc(N(C(=O)c2ccccc2F)S(=O)(=O)c2cc(OC)ccc2OC)cc1]

By "Compound 4" or "zb-179-4" is meant a compound having the formula shown below:

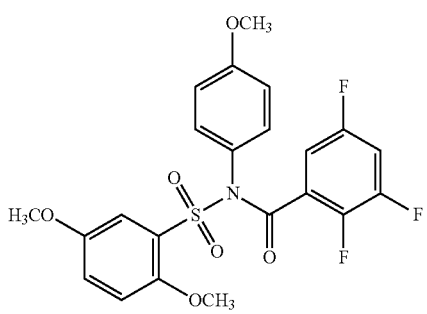 [SMILES: COc1ccc(N(C(=O)c2cc(F)cc(F)c2F)S(=O)(=O)c2cc(OC)ccc2OC)cc1]

By "Compound 5" or "zb-13-26" or "Zb26" is meant a compound having the structure shown below:

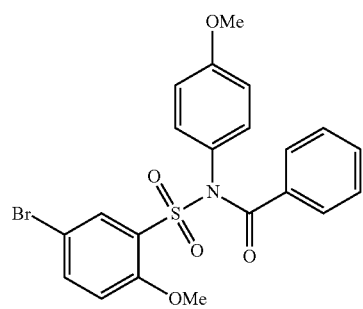 [SMILES: COc1ccc(N(C(=O)c2ccccc2)S(=O)(=O)c2cc(Br)ccc2OC)cc1]

By "Compound 6" is meant a compound having the structure shown below:

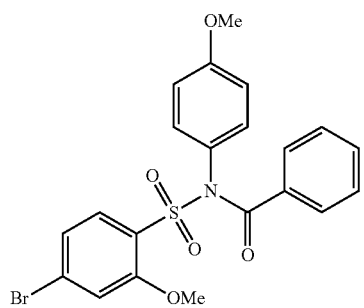 [SMILES: COc1ccc(N(C(=O)c2ccccc2)S(=O)(=O)c2ccc(Br)cc2OC)cc1]

By "Compound 7" is meant a compound having the structure shown below:

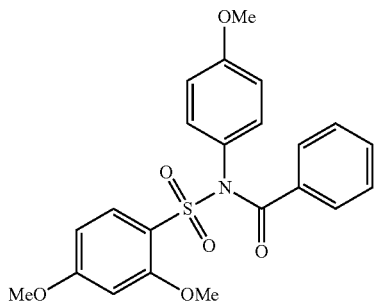 [SMILES: COc1ccc(N(C(=O)c2ccccc2)S(=O)(=O)c2ccc(OC)cc2OC)cc1]

By "Compound 8" is meant a compound having the structure shown below:

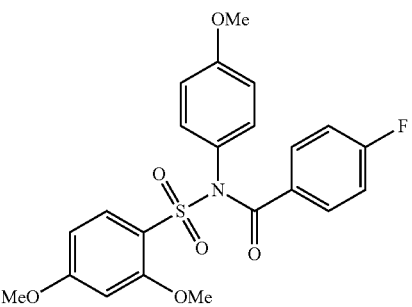 [SMILES: COc1ccc(N(C(=O)c2ccc(F)cc2)S(=O)(=O)c2ccc(OC)cc2OC)cc1]

By "Compound 9" is meant a compound having the structure shown below:

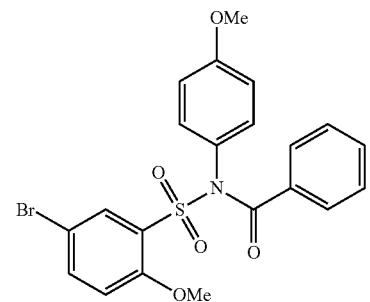

By "Compound 10" is meant a compound having the structure shown below:

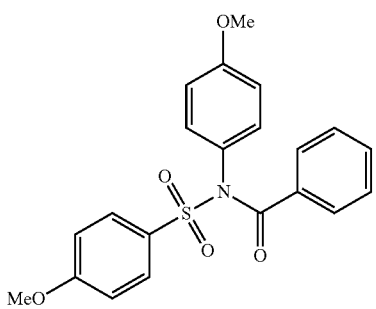 [SMILES: COc1ccc(N(C(=O)c2ccccc2)S(=O)(=O)c2ccc(OC)cc2)cc1]

By "Compound 11" is meant a compound having the structure shown below:

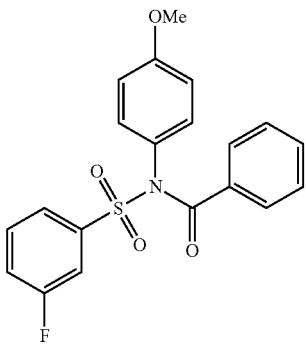 [SMILES: COc1ccc(N(C(=O)c2ccccc2)S(=O)(=O)c2cccc(F)c2)cc1]

By "Compound 12" is meant a compound having the structure shown below:

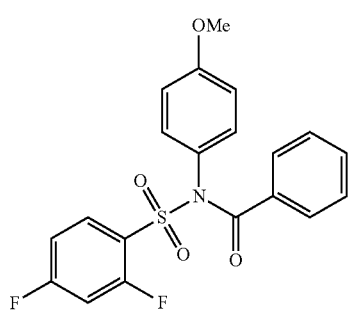 [SMILES: COc1ccc(N(C(=O)c2ccccc2)S(=O)(=O)c2ccc(F)cc2F)cc1]

By "Compound 13" is meant a compound having the structure shown below:

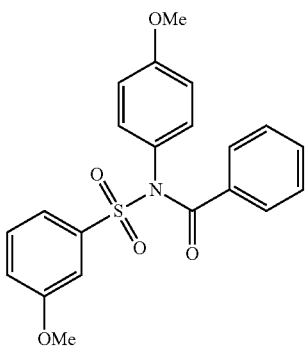 [SMILES: COc1ccc(N(C(=O)c2ccccc2)S(=O)(=O)c2cccc(OC)c2)cc1]

By "Compound 14" is meant a compound having the structure shown below:

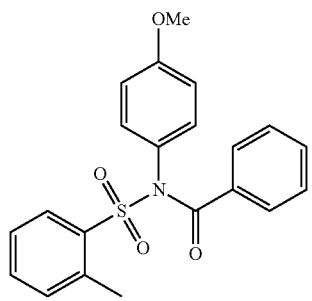 [SMILES: COc1ccc(N(C(=O)c2ccccc2)S(=O)(=O)c2ccccc2C)cc1]

By "Compound 15" is meant a compound having the structure shown below:

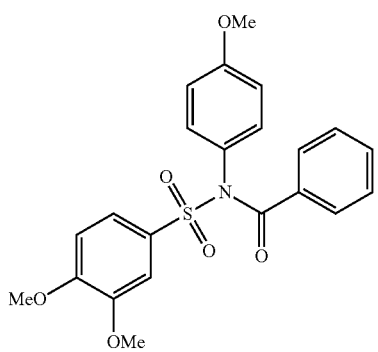 [SMILES: COc1ccc(N(C(=O)c2ccccc2)S(=O)(=O)c2ccc(OC)c(OC)c2)cc1]

In particular embodiments, a derivative of BRD9647 is Compound 1, 2, 3, 4, 5, 6, 7, 8, 9, 10, 11, 12, 13, 14, or 15.

By "benzoyl group" is meant a chemical group having the formula shown below:

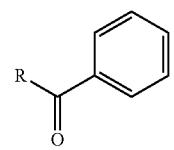

By "benzoylation" of an agent is meant the addition of a benzoyl group to an agent. In some embodiments, "benzoylation" may also refer to the addition of a benzoyl group with a functional group (e.g. fluorine, chlorine, bromine, iodine, etc.) attached at one or more (i.e., two, three, four, or five) carbon locations of the phenyl ring in a benzoyl group.

By "covalent modification" is meant modification of an agent by addition or removal of a chemical group on the agent. As used herein, "covalently modifying" an agent means adding or removing a chemical group on the agent. In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected. In particular embodiments, the analyte is a AZIN1 polynucleotide or polypeptide.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include multiple myeloma.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder. In particular embodiments, the marker is a AZIN1 polynucleotide or polypeptide.

As used herein, "obtaining" as in "obtaining an agent" includes synthesizing, purchasing, or otherwise acquiring the agent.

By "reduces" is meant a negative alteration of at least 10%, 25%, 50%, 75%, or 100%.

By "reducing cell survival" is meant negatively altering cell viability.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

As used herein, a "stroma-dependent" cell is a cell that is dependent on the presence of stromal cells for viability.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIGS. 1A-1D show that BRD9647 inhibited stroma-dependent multiple myeloma (MM) cells, but not most cell lines.

FIG. 1A is a schematic representation of the chemical structure of BRD9647.

FIG. 1B is a plot showing viability of multiple myeloma cell lines (primary MM, MOLP5 (with stroma), and MM1S (with stroma)) treated with various concentrations of BRD9647.

FIG. 1C shows in vitro test results indicating BRD9647 is selectively toxic to stroma-dependent myeloma cells.

FIG. 1D is a plot showing viability of ~100 cell lines from the Broad Institute CTD2 (Cancer Target Discover and Development) Center treated with various concentrations of BRD9647.

FIG. 1E is a plot showing the viability of MOLP5 treated with various concentrations of different fluoro-benzoyl analogs of BRD9647.

FIGS. 1F-1I show the structures of the fluorobenzoyl analogs used in the viability measurement.

FIG. 1F shows the molecular structure for Compound 1 (zb-179-3).

FIG. 1G shows the molecular structure for Compound 2 (zb-179-2).

FIG. 1H shows the molecular structure for Compound 3 (zb-16-14).

FIG. 1I shows the molecular structure for Compound 4 (zb-179-4).

FIGS. 2A-2C show that gene expression in BRD9647-sensitive cells treated with BRD9647 indicated endoplasmic reticulum (ER) stress or amino acid deprivation in the cells.

FIG. 2A is a heat map showing expression of genes in cells treated with BRD9647 and a control (DMSO). FIG. 2A shows sets of genes upregulated and downregulated in BRD9647-treated cells compared to cells treated with a control.

FIG. 2B is an enrichment plot showing results of a Gene Set Enrichment Analysis (GSEA) showing differential expression of the set of genes in FIG. 2A in cells under amino acid deprivation (HL-60 cells treated with CHR-2797 aminopeptidase inhibitor) versus a control.

FIG. 2C is a table showing the results of a Connectivity Map (CMap) analysis wherein a gene expression profile of interest was compared with a known gene expression profile to identify potential drugs showing a similar mechanism of action

FIG. 4A shows viability of MOLP5 cells resistant to ("MOLP5-R") and sensitive to ("MOLP5") BRD9647 treated with various concentrations of BRD9647.

FIGS. 4B-4C are plots showing results of sequencing of cDNA from MOLP5 cells sensitive to BRD9647 and MOLP5 cells resistant to BRD9647. BRD9647-sensitive MOLP5 cells harbored a mutation in AZIN1 (FIG. 4B), whereas BRD9647-resistant cells showed a loss of this mutation (FIG. 4C).

FIG. 4D are micrographs showing the viability of untreated MOLP5 cells and MOLP5 cells expressing AZIN1-WT or AZIN1-S367G treated with 13 µM BRD9647.

FIG. 5A shows the viability of MOLP5 cells treated with various concentrations of BRD9647. MOLP5 cells harboring an AZIN1 mutation ("MOLP5") were sensitive to BRD9647, and MOLP5 cells containing a wild-type AZIN1 gene that does not harbor the AZIN1 mutation ("MOLP5-AZIN1WT") were resistant to BRD9647 treatment.

FIGS. 5B-5C are plots showing results of sequencing of cDNA from MOLP5 cells sensitive to BRD9647 (which harbor the AZIN1 mutation) (FIG. 5B) and MOLP5 cells forced to overexpress a wild-type AZIN1 gene (FIG. 5C).

FIG. 7A shows viability of MOLP5 cells treated with various concentrations of BRD9647 in the presence or absence of spermidine. MOLP5 cells with 100 µM spermidine ("MOLP5+100 µM Spd"), and MOLP5 cells with 10 µM spermidine ("MOLP5+10 µM Spd"), each.

FIG. 7B depicts the structure of spermidine.

FIG. 7C depicts a reaction of BRD9647 with spermidine and structures of products of the reaction.

FIG. 10 shows that the portion of BRD9647 that penetrated the cell appeared to be unmodified, indicating that BRD9647 was likely not metabolite-reactive.

FIG. 13 is a table showing results of mass spectrometry of $^{13}$C-BRD9647 co-incubated with histones. The results show labeled lysines.

FIG. 15 is an immunoblot showing an increase in benzoylated lysines in cells following short and long term treatment with BRD9647.

DETAILED DESCRIPTION OF THE INVENTION

The invention features compositions and methods that are useful for treating multiple myeloma in a subject.

Figure 16:
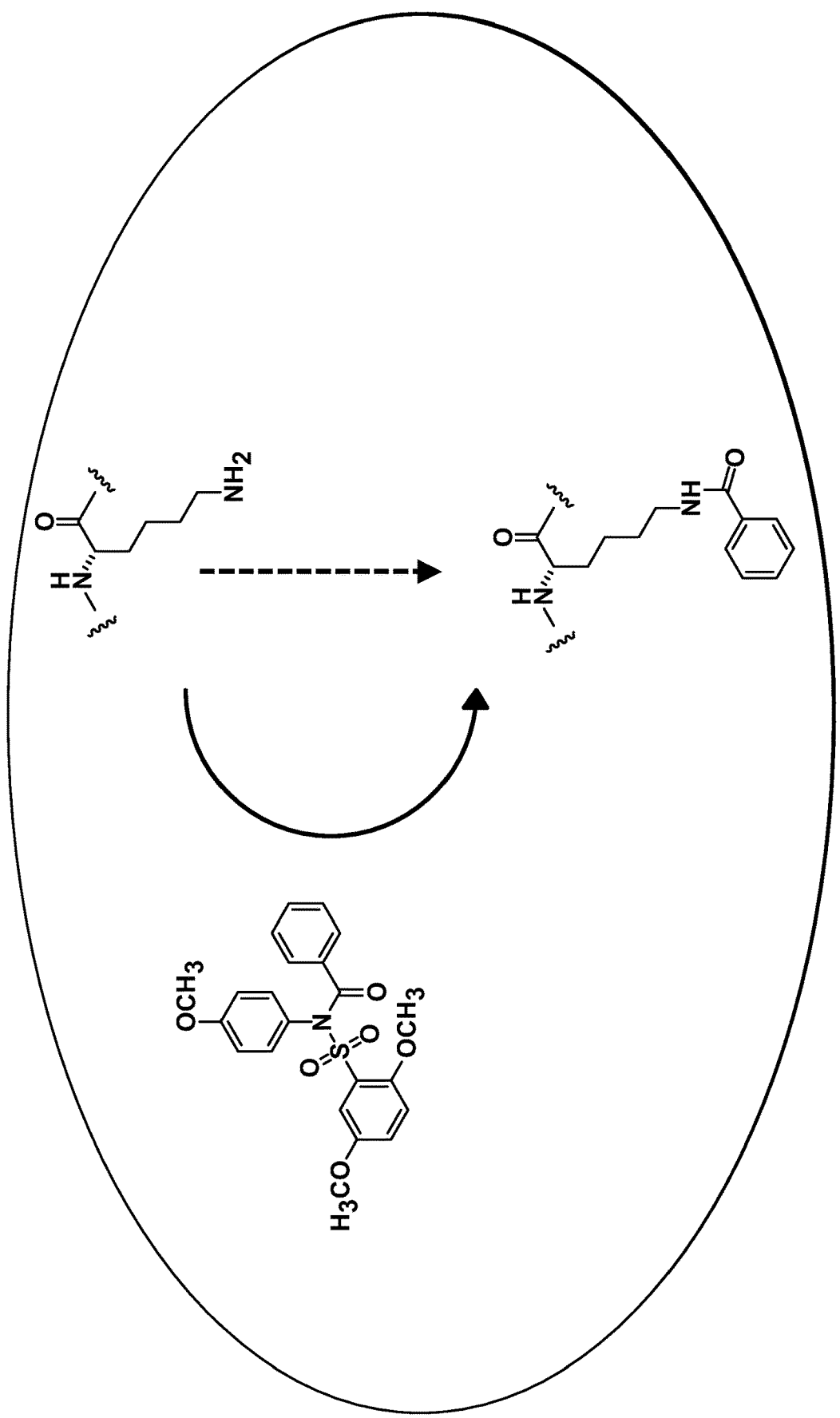
FIG. 16 is a schematic diagram showing that BRD9647-mediated benzoylation of cellular amines can be used therapeutically for the treatment of neoplasias having mutations in AZIN1.

The invention is based, at least in part, on the discovery that a compound (BRD9647) and certain derivatives thereof were selectively toxic to multiple myeloma cells that are dependent on normal stroma cells for viability. Without wishing to be bound by theory, BRD9647, and derivatives thereof, benzoylate cellular amines. Sensitivity to BRD9647 is conferred by the presence of an AZIN1 polypeptide comprising an S367G mutation. The invention is further based, at least in part, on the discovery that isotopically labeled BRD9647 was useful in probing benzoylation in a cell. FIG. 16 details a schematic diagram showing that BRD9647-mediated benzoylation of cellular amines can be used therapeutically for the treatment of neoplasias having mutations in AZIN1. Without wishing to be bound by theory, neoplasias containing AZIN1 mutation alter polyamine regulation and therefore are susceptible to BRD9647-mediated benzoylation of cellular amines. This includes benzoylation of amine-containing metabolites and benzoylation of amine-containing amino acids like lysines on polypeptides. Accordingly, the invention features compositions and methods for characterizing benzoylation in a cell.

BRD9647

Multiple myeloma (MM) screening identified BRD9647 as a compound selective for MM cells that are dependent on normal stromal cells for viability. BRD9647 was found to be a benzoyl donor for nucleophiles, such as amine-containing biomolecules. Confirmation of this benzoyl donor ability was done using physiological amines (polyamines) and purified proteins using a $^{13}$C-labeled analog via NMR and mass spectrometry. The compound was confirmed to be a benzoyl donor in cells using a $^{14}$C-labeled analog.

Without being bound by theory, the data described herein indicate that benzoylation is a post-translational modification of amine-containing amino acids. Agents, such as BRD9647 and derivatives thereof, that perturb benzoylation of cellular amines inhibited the growth of multiple myeloma cells comprising an AZIN1 mutation, which have altered cellular polyamine regulation, and are useful for the treatment of cancers. Accordingly, the present invention features methods of inhibiting proliferation of a multiple myeloma cell, the method comprising contacting the cell with BRD9647, thereby inhibiting proliferation of the cell. In some embodiments, the method of inhibiting proliferation of a multiple myeloma cell comprises covalently modifying a residue of a polypeptide in the cell, wherein the modification is addition or removal of a benzoyl group.

Analogs of BRD9647

The present disclosure also provides analogs of BRD9647 which may be used as benzoyl or functionalized benzoyl donors to multiple myeloma cells. These analogs of BRD9647 may provide an alternate therapeutic benefit in the treatment of multiple myeloma as compared to BRD9647. For example, some analogs of BRD9647 may provide increased or decreased growth inhibition of MM cells at each concentration as compared to BRD9647.

Some analogs of BRD9647 have the structure of formula (I):

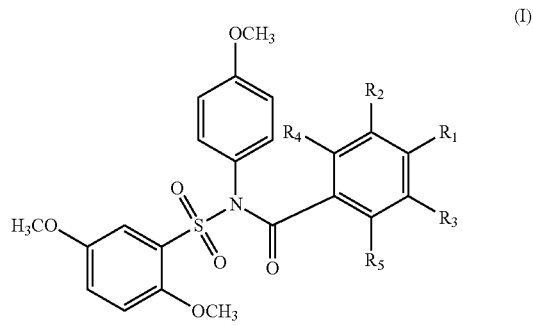

wherein $R_1$-$R_5$ are each independently selected from hydrogen, —F; —Cl; —Br; —I; —R*; —OH; —OR*; —NH$_2$; —NHR*; —N(R*)$_2$; —N(R*)$_3^+$; —N(R*)—OH; —N(→O)(R*)$_2$; —O—N(R*)$_2$; —N(R*)—O—R*; —N(R*)—N(R*)$_2$; —C≡N—R*; —N═C(R*)$_2$; —C═N—N(R*)$_2$; —C(═NR*)(—N(R*)$_2$); —C(H)(═N—OH); —SH; —SR*; —CN; —NC; —C(═O)—R*; —CHO; —CO$_2$H; —CO$_2$—; —CO$_2$R*; —C(═O)—S—R*; —O—(C═O)—H; —O—(C═O)—R*; —S—C(═O)—R*; —(C═O)—NH$_2$; —C(═O)—N(R*)$_2$; —C(═O)—NHNH$_2$; —C(═O)—NHNH$_2$; —C(═S)—NH$_2$; —(C═S)—N(R*)$_2$; —N(R*)—CHO; —N(R*)—C(═O)—R*; —C(═NR*)—O—R*; —O—C(═NR*)—R*; —SCN; —NCS; —NSO; —SSR*; —N(R*)—C(═O)—N(R*)$_2$; —N(R*)—C(═S)—N(R*)$_2$; —S(═O)$_{1-2}$—R*; —O—S(═O)$_2$—R*; —S(═O)$_2$—OR*; —N(R*)—S(═O)$_2$—R*; —S(═O)$_2$—N(R*)$_2$; —O—SO$_3$; —O—S(═O)$_2$—OR*; —O—S(═O)—OR*; —O—S(═O)—R*; —S(═O)—OR*; —S(═O)—R*; —NO; —NO$_2$; —NO$_3$; —O—NO; —O—NO$_2$; —N$_3$; —N$_2$—R*; —N(C$_2$H$_4$); —Si(R*)$_3$; —CF$_3$; —O—CF$_3$; —O—CH$_3$; —O—(CH$_2$)$_{1-6}$CH$_3$; —PR*$_2$; —O—P(═O)(OR*)$_2$; and —P(═O)(OR*)$_2$;

R* is, independently at each occurrence from hydrogen, and a $C_{1-10}$ (e.g., $C_{1-8}$ or $C_{1-6}$ or $C_{1-4}$) hydrocarbon (e.g., alkyl, alkenyl, alkynyl, aryl (e.g., phenyl), alkyl-aryl (e.g., benzyl), aryl-alkyl (e.g., toluyl), etc.); where at least one of $R_1$-$R_5$ is not hydrogen;

or pharmaceutically acceptable salts thereof.

Other analogs of BRD9647 have the structure of formula (II):

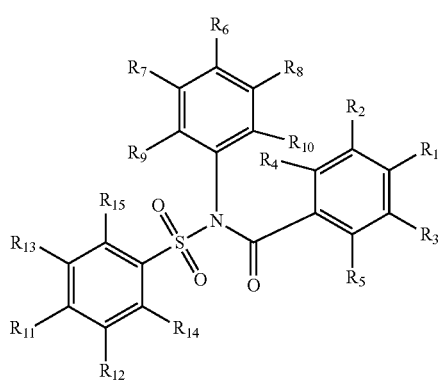

(II)

wherein $R_1$-$R_{15}$ are each independently selected from hydrogen, —F; —Cl; —Br; —I; —R*; —R*; —OH; —OR*; —NH$_2$; —NHR*; —N(R*)$_2$; —N(R*)$_3^+$; —N(R*)—OH; —N(→O)(R*)$_2$; —O—N(R*)$_2$; —N(R*)—O—R*; —N(R*)—N(R*)$_2$; —C=N—R*; —N=C(R*)$_2$; —C=N—N(R*)$_2$; —C(=NR*)(—N(R*)$_2$); —C(H)(=N—OH); —SH; —SR*; —CN; —NC; —C(=O)—R*; —CHO; —CO$_2$H; —CO$_2$—; —CO$_2$R*; —C(=O)—S—R*; —O—(C=O)—H; —O—(C=O)—R*; —S—C(=O)—R*; —(C=O)—NH$_2$; —C(=O)—N(R*)$_2$; —C(=O)—NHNH$_2$; —O—C(=O)—NHNH$_2$; —C(=S)—NH$_2$; —(C=S)—N(R*)$_2$; —N(R*)—CHO; —N(R*)—C(=O)—R*; —C(=NR*)—O—R*; —O—C(=NR*)—R*; —SCN; —NCS; —NSO; —SSR*; —N(R*)—C(=O)—N(R*)$_2$; —N(R*)—C(=S)—N(R*)$_2$; —S(=O)$_{1-2}$—R*; —O—S(=O)$_2$—R*; —S(=O)$_2$—OR*; —N(R*)—S(=O)$_2$—R*; —S(=O)$_2$—N(R*)$_2$; —O—SO$_3$; —O—S(=O)$_2$—OR*; —O—S(=O)—OR*; —O—S(=O)—R*; —S(=O)—OR*; —S(=O)—R*; —NO; —NO$_2$; —NO$_3$; —O—NO; —O—NO$_2$; —N$_3$; —N$_2$—R*; —N(C$_2$H$_4$); —Si(R*)$_3$; —CF$_3$; —O—CF$_3$; —O—CH$_3$; —O—(CH$_2$)$_{1-6}$CH$_3$; —PR*$_2$; —O—P(=O)(OR*)$_2$; and —P(=O)(OR*)$_2$;

R* is, independently at each occurrence from hydrogen, and a $C_{1-10}$ (e.g., $C_{1-8}$ or $C_{1-6}$ or $C_1$-4) hydrocarbon (e.g., alkyl, alkenyl, alkynyl, aryl (e.g., phenyl), alkyl-aryl (e.g., benzyl), aryl-alkyl (e.g., toluyl), etc.).

Compound Forms and Salts

The compounds of the present invention include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include $C_{1-6}$ alkyl esters of carboxylic acid groups, which, upon administration to a subject, are capable of providing active compounds.

Pharmaceutically acceptable salts of the compounds of the present disclosure include those derived from pharmaceutically acceptable inorganic and organic acids and bases. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient.

Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the present invention and their pharmaceutically acceptable acid addition salts. Salts derived from appropriate bases include alkali metal (e.g., sodium), alkaline earth metal (e.g., magnesium), ammonium and N-(alkyl)$_4^+$ salts. The present invention also envisions the quaternization of any basic nitrogen-containing groups of the compounds disclosed herein. Water or oil-soluble or dispersible products may be obtained by such quaternization. Salt forms of the compounds of any of the formulae herein can be amino acid salts of carboxyl groups (e.g., L-arginine, -lysine, -histidine salts).

Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8] each of which is incorporated herein by reference in their entireties.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the present invention.

The present invention also includes various hydrate and solvate forms of the compounds.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Companion Diagnostics

The present invention features assays for the characterization of cancer (e.g., multiple myeloma) for responsiveness to treatment with BRD9647 or a derivative thereof. In one embodiment, an AZIN1 polynucleotide or polypeptide is characterized for the presence of a mutation (e.g., S367G or any mutation that increases antizyme binding or inhibitory activity). The presence of a mutation in an AZIN1 polypeptide or polynucleotide is detected by standard methods, such as sequencing RNA or complementary DNA, probe hybridization, antibody binding, or any other method known in the art. In another embodiment, an AZIN1 polypeptide is characterized for antizyme binding or inhibiting activity.

Types of Biological Samples

In characterizing the responsiveness of a malignancy (e.g., multiple myeloma) in a subject to treatment with BRD9647 or a derivative thereof, the sequence or activity of AZIN1 is measured, for example, in a biologic sample of a subject, such as a tumor sample. The presence of AZIN1 having a mutation (e.g., S367G) that increases antizyme binding or inhibiting activity indicates that the malignancy is responsive to treatment with BRD9647 or a derivative thereof.

Selection of a Treatment Method

As reported herein below, subjects suffering from a malignancy (e.g., multiple myeloma) may be tested for an AZIN1 in the course of selecting a treatment method. Patients characterized as having a mutation in AZIN1 (e.g., S367G) are identified as responsive to treatment with BRD9647 or a derivative thereof.

Treatment of Multiple Myeloma with BRD9647

The studies described herein revealed that benzoylation of protein amines and organic amines is a novel therapeutic approach to target certain cancer cells. Accordingly, the present invention provides methods of treating multiple myeloma or disorders or symptoms thereof which comprise administering a therapeutically effective amount of a pharmaceutical composition comprising a BRD9647 to a subject (e.g., a mammal such as a human). One embodiment is a method of treating a subject suffering from or susceptible to multiple myeloma. In particular embodiments, the multiple myeloma is stroma-dependent. The method includes the step of administering to the mammal a therapeutic amount of BRD9647 sufficient to treat the disease or disorder or symptom thereof, under conditions such that the disease or disorder is treated.

The methods herein include administering to the subject (including a subject identified as in need of such treatment) an effective amount of a BRD9647, or a composition described herein to produce such effect. Identifying a subject in need of such treatment can be in the judgment of a subject or a health care professional and can be subjective (e.g. opinion) or objective (e.g. measurable by a test or diagnostic method).

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of BRD9647 to a subject (e.g., animal, human) in need thereof, including a mammal, particularly a human. Such treatment will be suitably administered to subjects, particularly humans, suffering from, having, susceptible to, or at risk for multiple myeloma. In particular embodiments, the BRD9647 is administered to a subject having a multiple myeloma. In particular embodiments, the multiple myeloma is stroma-dependent.

Determination of those subjects "at risk" can be made by any objective or subjective determination by a diagnostic test or opinion of a subject or health care provider (e.g., genetic test (particularly, genetic test for an AZIN1 mutation), enzyme or protein marker, family history, and the like). The BRD9647 compositions herein may be also used in the treatment of any other disorders in which the AZIN1 mutation or benzoylation of proteins may be implicated.

In some embodiments, a subject is selected for treatment with BRD9647 by detection of a AZIN1 mutation relative to a reference in a biological sample obtained from the subject. The sample obtained from the subject may be a blood sample. In particular embodiments, the AZIN1 mutation is S367G. The reference AZIN1 sequence may be a wild-type AZIN1 sequence or an AZIN1 polypeptide or polynucleotide sequence of AZIN1 in a BRD9647-resistant cell line (e.g., in a stroma independent multiple myeloma cell line, or a BRD9647-resistant cell line identified in studies described herein). Methods for detecting a AZIN1 mutation in the sample include immunoassay, direct sequencing of RNA or complementary DNA, and probe hybridization to a polynucleotide encoding the mutant polypeptide.

The present invention further provides a therapeutic composition comprising BRD9647. The administration of a therapeutic composition comprising BRD9647 may be by any suitable means that results in a concentration of the therapeutic that, combined with other components, is effective in ameliorating, reducing, or stabilizing multiple myeloma in a patient. The therapeutic composition comprising BRD9647 may be administered systemically, for example, formulated in a pharmaceutically-acceptable buffer such as physiological saline. Routes of administration include, for example, subcutaneous, intravenous, interperitoneally, intramuscular, or intradermal injections that provide continuous, sustained levels of the drug in the patient.

Treatment of human patients or other animals is carried out using a therapeutically effective amount of BRD9647 in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of multiple myeloma. Generally, amounts will be in the range of those used for other agents used in the treatment of multiple myeloma, although in certain instances lower amounts will be needed because of the increased specificity of the compound. The therapeutic composition is administered at a dosage that ameliorates the multiple myeloma and/or symptoms thereof as determined by a method known to one skilled in the art.

Combination Therapies

In some embodiments, the therapeutic composition comprising BRD9647 may be administered to a subject having multiple myeloma, in combination with any other standard therapy for the disease. Standard therapy for multiple myeloma include, for example, chemotherapy, radiation therapy, and surgery.

Probes and Method for Probing Benzoylation in Cells

The present invention features compositions and methods useful for probing covalent modifications, particularly benzoylation, of agents (e.g., polypeptides or metabolites) in a cell. Described herein is a study of a compound, BRD9647 (an N-benzoyl sulfonamide), with the capacity to selectively kill certain cancer cell-lines. Without being bound by theory, it is hypothesized that BRD9637 exerts its effects through covalent modification of nucleophilic residues of a biological system. In particular, the benzoyl group transfer from sulfonamide to a more nucleophilic nitrogen (i.e., lysine, free polyamines, etc.) reasonably explained the observed activity. In the study described herein, several isotopic labels were utilized to probe the fate of BRD9637 in a complex cellular setting: a) $^{13}$C-labeled carbonyl demonstrated reactivity with relevant amine-containing metabolites; b) $^{14}$C-labeled BRD9637 aided in localizing the compound through radioactivity-guided cellular fractionation (this probe also validated BRD9637's ability to benzoylate purified proteins (histone, BSA) in vitro); and, c) $D_5$-labeled BRD9637 can be used for unbiased quantitative mass spectrometric analysis of direct protein targets.

The studies described herein demonstrated that isotopic labeling of compounds that covalently interact with their cellular targets is a powerful tool for elucidating its mechanism of action. This strategy obviates the need to search for chemical alterations that would allow for installation of more structurally-compromising chemical handles. Accordingly, the present invention provides compositions comprising isotopically labeled BRD9637. The present invention also provides methods of for probing benzoylation of agents in a cell using isotopically labeled BRD9637.

In particular embodiments, the detectable label on BRD9647 is an isotopic label. In particular embodiments, the isotopic label is on the benzoyl group of BRD9647. In particular embodiments, the isotopic label is a $^{13}$C, $^{14}$C, or $D_5$. The isotopically labeled group (e.g. the benzoyl group on BRD9647) is transferred to a substrate in a benzoylation reaction with BRD9647 as a benzoyl donor. The benzoylated substrate is then detected by detection of the isotopic label. The isotopic label may be detected by any suitable method (e.g., autoradiography, mass spectrometry, or nuclear magnetic resonance).

Detection of benzoylated substrates in a cell is useful for investigating substrates for benzoylation and cellular mechanisms implicating benzoylation of agents (e.g. polypeptides, nuclei acid molecules, or metabolites) in a cell. Accordingly, the present invention provides a method characterizing benzoylation of an agent in a cell, the method comprising contacting the cell with the composition comprising a labeled BRD9637, and measuring benzoylation of the agent by detecting a detectable label on the agent. In other aspects, the present invention provides a method of modulating benzoylation of an agent in a cell. In some aspects, the present invention provides a method of identifying an agent in a cell that is a substrate for benzoylation. The method comprises contacting the cell with BRD9647 or a composition comprising labeled BRD9647, and measuring benzoylation of the agent relative to a reference, wherein an alteration in benzoylation indicates that the agent is a substrate for benzoylation. The reference may be a benzoylation level of an agent in a control cell (e.g., a cell not treated with BRD9647).

Perturbation of biological systems with exogenous materials is a mainstay of the biopharmaceutical enterprise. A simple act of adding a small molecule to cells in vitro leads to numerous interactions that together constitute the compound's mechanism of action. The compositions and methods featured in the present invention are useful for understanding these complex interactions, which is crucial for furthering compounds that emerge from phenotypic screens and for optimizing the compound's ability to alter biological states in desired directions.

Kits

The invention provides kits for the treatment or prevention of multiple myeloma (in particular, stroma-dependent multiple myeloma). In one embodiment, the kit includes a therapeutic or prophylactic composition containing an effective amount of BRD9647. In some embodiments, the kit includes a therapeutic or prophylactic composition containing an effective amount of BRD9647 and a capture reagent detecting an AZIN1 polypeptide or polynucleotide. The capture reagent, for example, may be a hybridization probe for an AZIN1 polynucleotide or primers for direct sequencing of an AZIN1 polynucleotide. In some embodiments, the kit comprises a sterile container which contains the therapeutic or prophylactic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired, the therapeutic or prophylactic composition is provided together with instructions for administering the BRD9647 to a subject having or at risk of developing multiple myeloma. The instructions will generally include information about the use of the composition for the treatment or prevention of the disease. In other embodiments, the instructions include at least one of the following: description of BRD9647; dosage schedule and administration for treatment or prevention of multiple myeloma or related conditions or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The invention further provides kits for probing benzoylation of agents (e.g. polypeptides, nucleic acid molecules, or metabolites) in a cell. The kit comprises a detectably labeled BRD9647. In particular embodiments, the detectable label is an isotopic label. In particular embodiments, the isotopic label is on the benzoyl group of BRD9647. In some embodiments, the kit further includes other reagents, including, for example, reagents for incubating cells with BRD9647 or preparing cells for treatment with BRD9647, reagents for preparing cell extracts. In some embodiments, the kit may further include capture reagents for detection of other analytes in a cell.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Figure 1A:
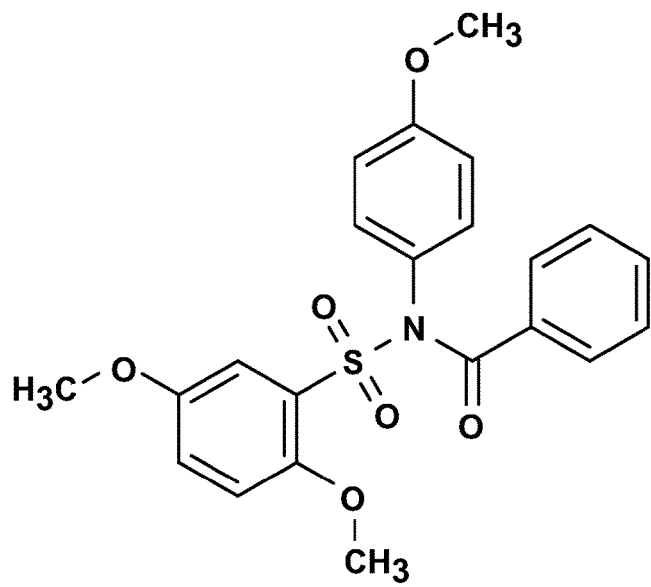
Figure 1B:
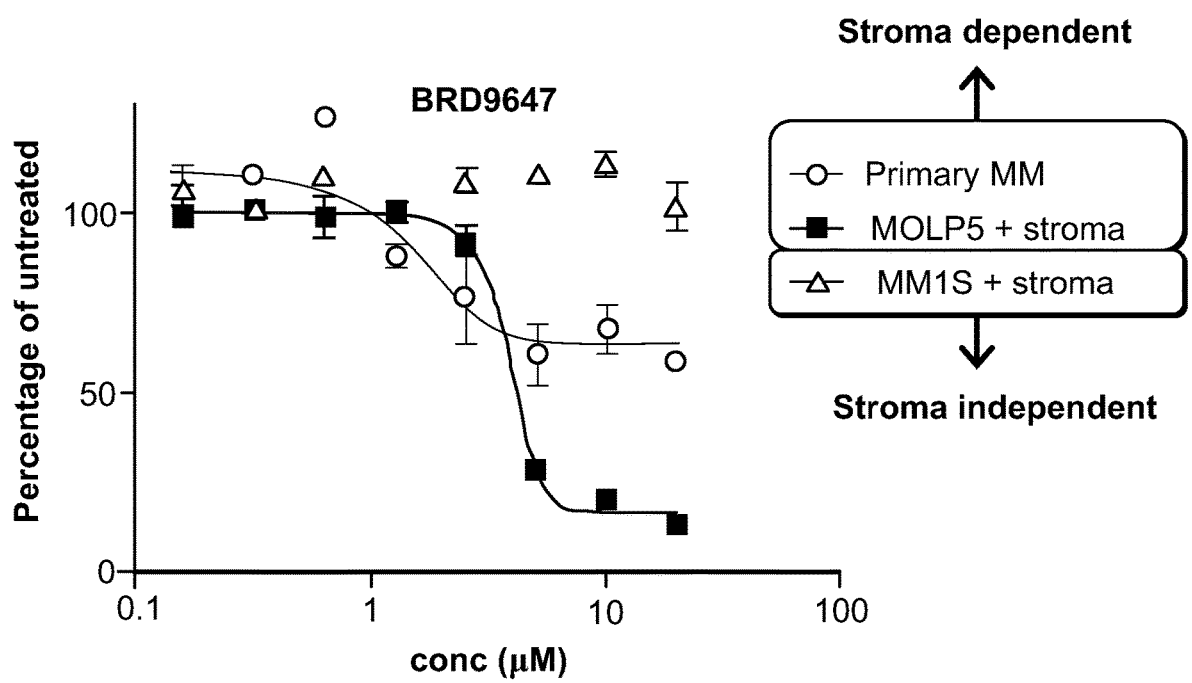
Figure 1D:
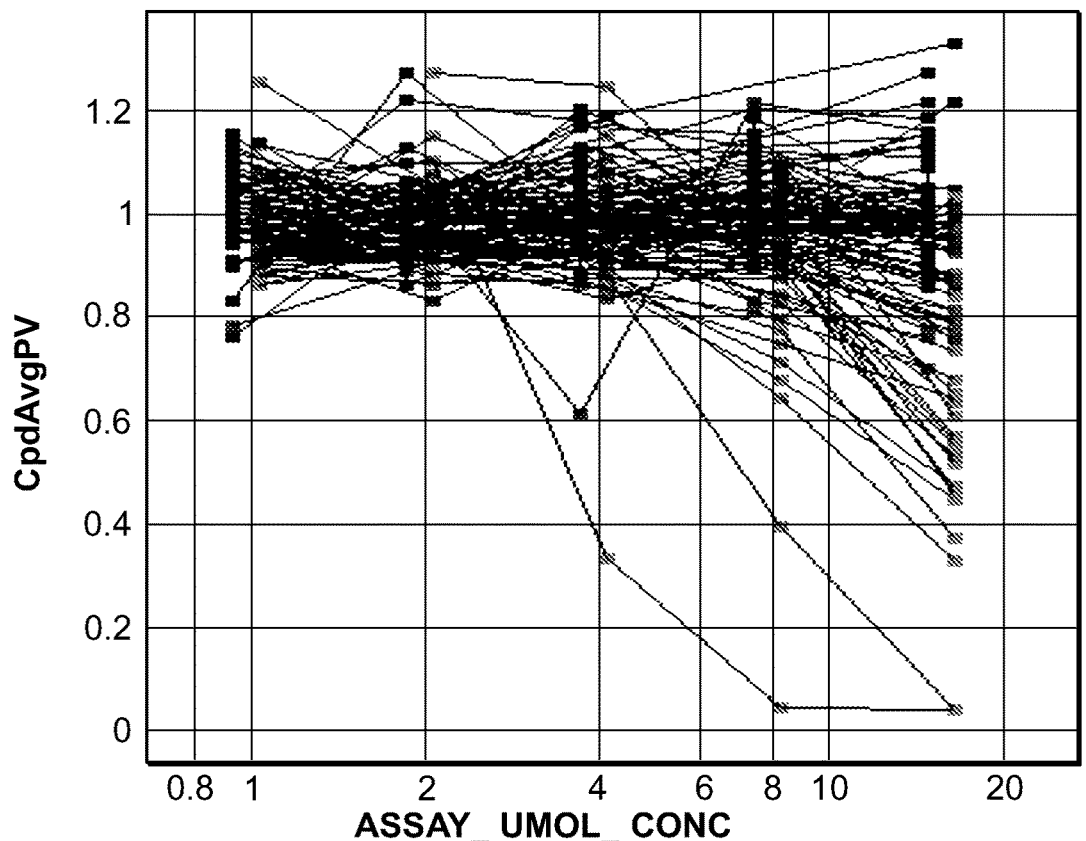

Example 1: BRD9647 Selectively Inhibited Growth of Stroma-Dependent Multiple Myeloma Cells BRD9647 was identified in a phenotypic screening of multiple myeloma cells as a growth inhibitor of certain stroma-dependent myeloma cells. FIG. 1A shows the chemical structure of BRD9647. FIG. 1B is a plot showing viability of multiple myeloma cell lines (primary multiple myeloma (primary MM) cells (with stroma), MOLP5 (with stroma), and MM1S (with stroma)) treated with various concentrations of BRD9647. For these experiments GFP-labeled MOLP5 and MM1S cells were co-cultured with unlabeled primary human bone marrow stromal cells in 384-well plates and exposed to increasing concentrations of BRD9647 for 3 days. At the end of this period, wells were imaged in the GFP channel with the IXMicro automated high-throughput microscope (Molecular Devices), remaining GFP positive cells were quantified using the MetaXpress software (Molecular Devices) and expressed as percentages of DMSO (vehicle) controls. Unlabeled primary MM cells were similar treated with BRD9647 but were stained with the calcein-acetoxymethyl ester dye at the end of the treatment period. The dye fluoresces green inside viable cells that contain esterase enzymes. Viable cells were imaged and quantified similar to GFP-positive myeloma cell-lines using size, shape and staining intensity to distinguish primary MM from stromal cells. FIG. 1C depicts images showing the viability of primary MM and MOLP5 myeloma cell lines that received BRD9647 treatment in the presence and absence of stromal co-culture. These data indicate that BRD9647 is selectively toxic to stroma-dependent myeloma cells. FIG. 1D is a plot showing viability of ~100 cell lines from the Broad Institute CTD2 (Cancer Target Discover and Development) Center treated with various concentrations of BRD9647. Viable cells in these experiments after 3 days of compound exposure were measured using the Cell Titer Glo reagent (Promega). As shown in FIG. 1D, BRD9647 inhibited stroma-dependent multiple myeloma (MM) cells, but not most cell lines.

Figure 2A:
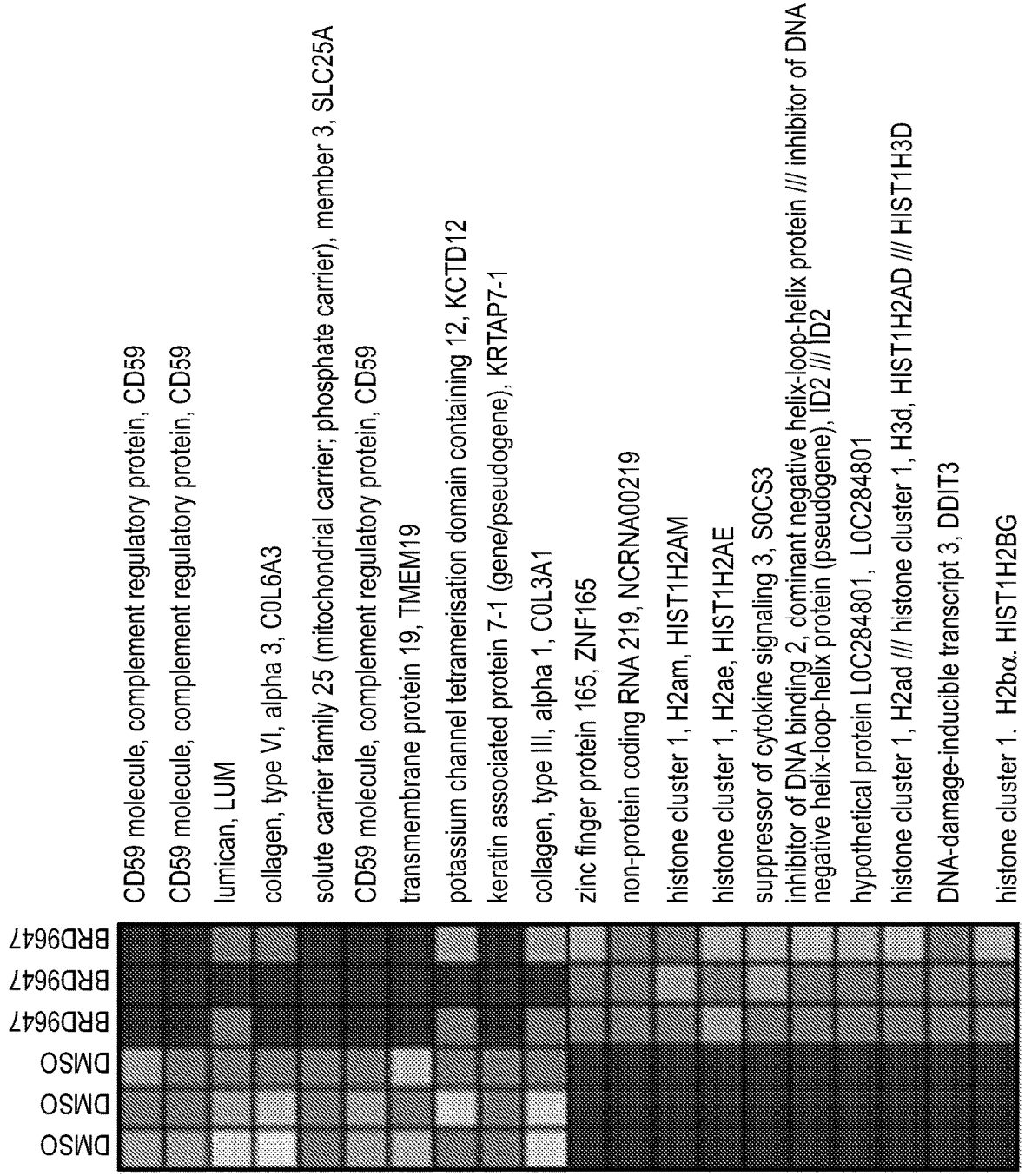
Figure 2B:
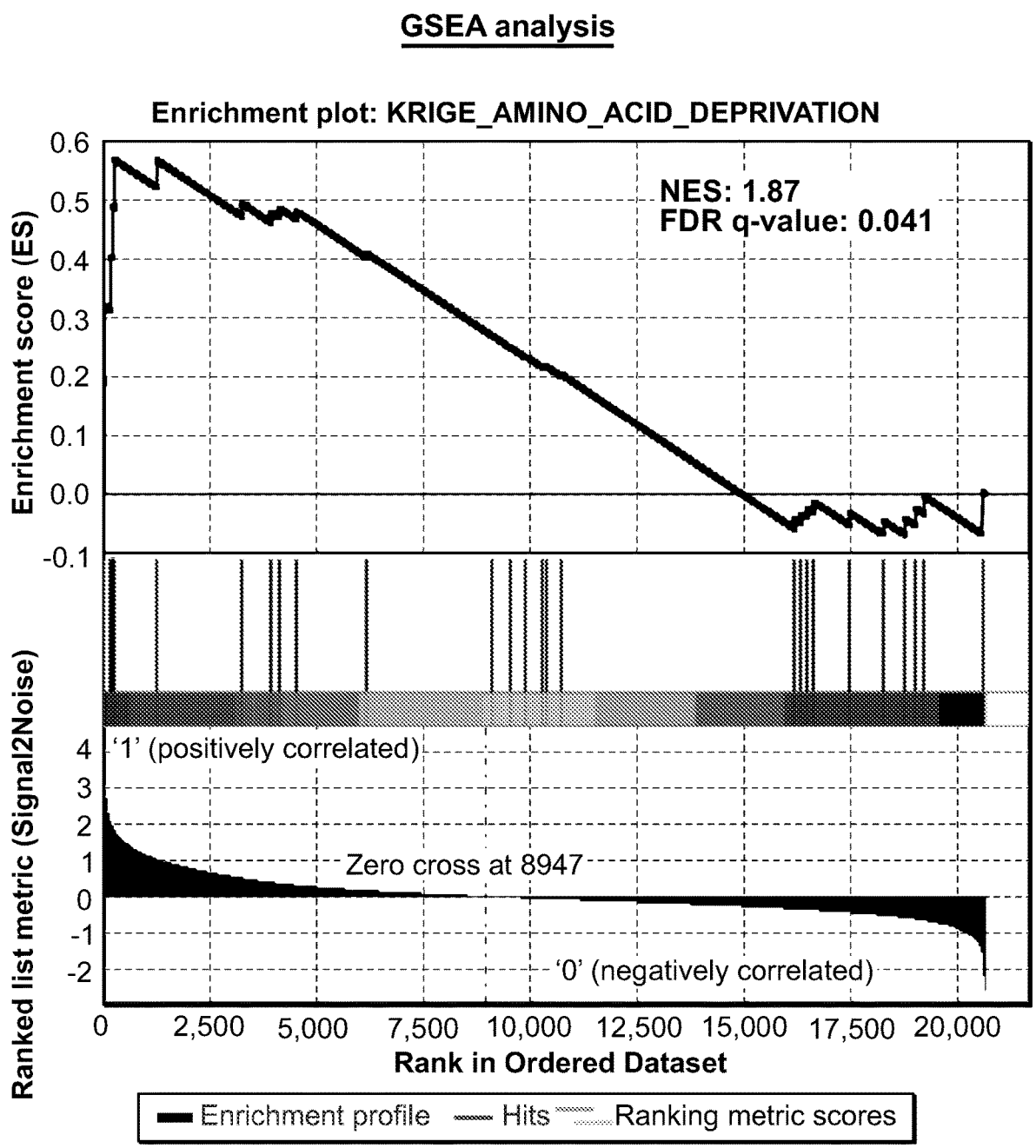

Gene-expression analysis identified endoplasmic reticulum (ER) stress as an effect of BRD9647 in BRD9647-sensitive cells. FIGS. 2A-2C show that gene expression in BRD9647-sensitive cells treated with BRD9647 indicated endoplasmic reticulum (ER) stress or amino acid deprivation in the cells. FIG. 2A shows upregulation or downregulation of sets of genes in cells treated with BRD9647 relative to a control (DMSO). For this experiment, MOLP5 cells were exposed to DMSO or 10 μM BRD9647 for 6 hours then subject to total RNA extraction using the TRIzol reagent (Thermo-Fisher). RNA was then hybridized to the Affymetrix U133 2.0 Plus oligonucleotide microarray (Affymetrix) and relative transcripts quantified following the manufacturer's protocol. Differential gene expression analysis was conducted using the Comparative Marker Selection module of GenePattern software (www.broadinstitute.org/genepattern). Genes upregulated or downregulated in BRD9647-treated cells in FIG. 2A showed similarities to differential expression in cells under amino acid deprivation (HL-60 cells treated with CHR-2797 aminopeptidase inhibitor) versus a control (FIG. 2B) For this experiment, gene expression analysis from FIG. 2A was subjected to Gene Set enrichment Analysis (www.broadinstitute.org/gsea) that measures enrichment of gene sets, derived from over 10,000 experimental conditions, in a particular gene expression profile. These results indicate that BRD9647-sensitive cells treated with BRD9647 were under ER stress or amino acid deprivation. As show in FIG. 2C, Connectivity Map (CMap) analysis was conducted (www.broadinstitute.org/cmap) to compare a gene expression profile of BRD9657 with known gene expression profiles of over 5000 compounds to identify potential drugs showing a similar mechanism of action. Protein synthesis inhibitors of interest identified by the analysis are shown in boxes (FIG. 2C).

Example 2: Synthesis of BRD9647 Analog Compound 5

NMR spectra were recorded on a Bruker 400 (400 MHz 1H, 100 MHz 13C) spectrometer. Proton and carbon chemical shifts are reported in ppm (δ) referenced to the NMR solvent. Data are reported as follows: chemical shifts, multiplicity (br=broad, s=singlet, t=triplet, q=quartet, m=multiplet; coupling constant (s) in Hz). Unless otherwise indicated NMR data were collected at 25° C. Flash chromatography was performed using 100-200 mesh Silica Gel. Liquid Chromotography/Mass Spectrometry (LCMS) was performed on Agilent1200HPLC and 6110MS.

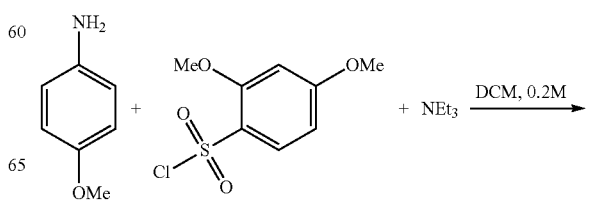

-continued

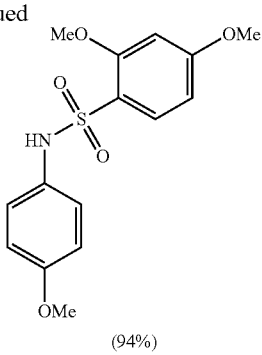

(94%)

2,5-dimethoxybenzene-1-sulfonyl chloride (2 g, 8.45 mmol, 1 equiv) was added to a round-bottom flask containing 4-methoxyaniline (1.04 g, 8.45 mmol, 1 equiv), and triethylamine (3.53 mL, 25.4 mmol, 3 equiv) dissolved in DCM (42.3 mL, 0.2 M). The reaction was allowed to stir at room temperature until completion (several hours). Crude reaction mixture was evaporated and purified by flash column chromatography on silica gel (methanol in DCM, 0-5%) to yield 94% (2.56 g, 7.91 mmol) of the product sulfonamide as characterized by LCMS and NMR. NMR spectra of were measured using chloroform-d and a frequency of 400 mHz resulting in chemical shifts of δ (ppm)= 7.27 (d, J=3.1 Hz, 1H), 7.07-6.95 (m, 4H), 6.73 (d, J=9.3 Hz, 2H), 4.03 (s, 3H), 3.76-3.65 (m, 6H), 1.14 (s, 1H).

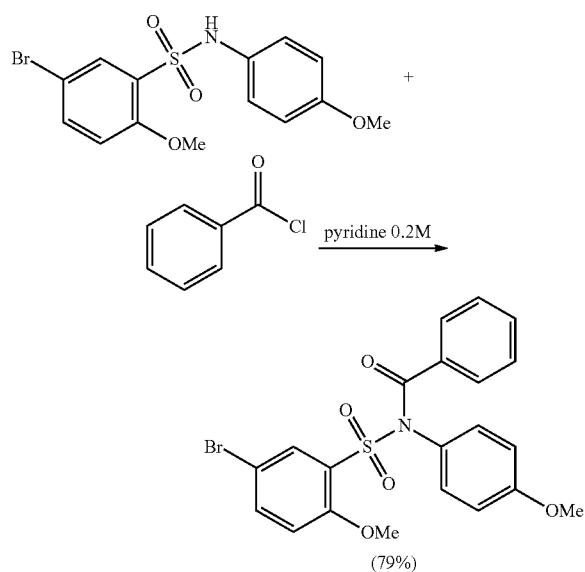

(79%)

5-bromo-2-methoxy-N-(4-methoxyphenyl)benzenesulfonamide (3.78 g, 10, 15 mmol, 1 equiv) was dissolved in pyridine (50.8 mL, 0.2 M). Benzoyl chloride (1.30 mL, 11.17 mmol, 1.1 equiv) was added to this solution, and the mixture was allowed to stir at room temperature until the reaction was complete. The reaction mixture was then diluted with DCM, and partitioned between 1 M HCl. The organic fraction was evaporated and purified by flash column chromatography on silica with methanol in DCM (0-5%) to yield 79% (3.79 g) of the product. NMR spectra of were measured using DMSO-d6 and a frequency of 400 mHz resulting in chemical shifts of δ (ppm)=8.02 (d, J=2.7 Hz, 1H), 7.91 (dd, J=8.9, 2.7 Hz, 1H), 7.44-7.19 (m, 8H), 6.96-6.85 (m, 2H), 3.88 (s, 3H), 3.73 (s, 3H). $^{13}$C NMR (101 MHz, DMSO) δ 169.1, 159.4, 155.8, 138.5, 133.9, 133.5, 132.2, 131.3, 128.4, 128.2, 128.2, 128.1, 115.8, 114.0, 111.0, 56.6, and 55.3.

Synthesis of BRD9647 Deuterated Analog

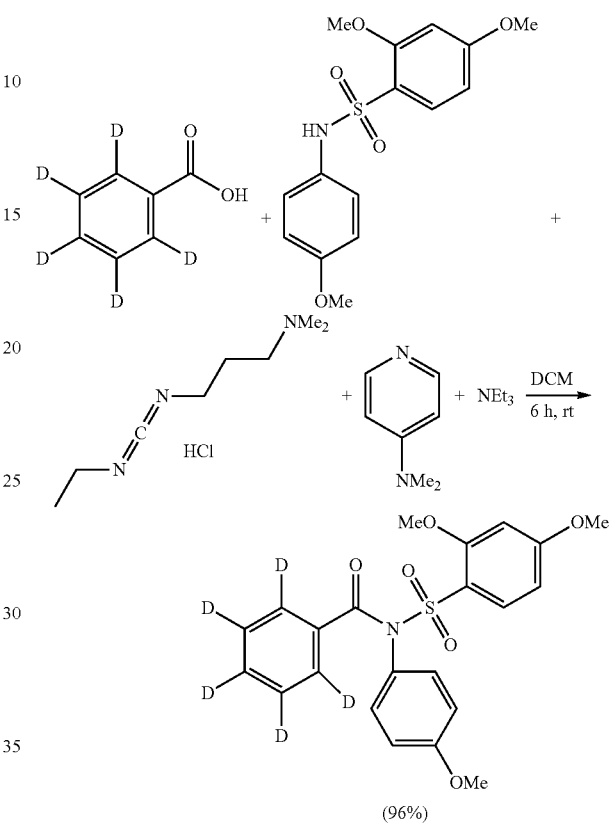

(96%)

2,5-dimethoxy-N-(4-methoxyphenyl)benzenesulfonamide (112 mg, 0.35 mmol, 1 equiv), benzoic acid-d5 (66.1 mg, 0.52 mmol, 1.5 equiv), EDCI HCl (146 mg, 0.76 mmol, 2.2 equiv), DMAP (93 mg, 0.76 mmol, 2.2 equiv), and triethylamine (145 uL, 1.04 mmol, 3 equiv) were dissolved in DCM (1.73 mL, 0.2 M) and stirred or shaken at room temperature for 6 hours. Following evaporation of volatiles, flash column chromatography on silica gel with methanol in DCM (0-5%) was applied to the mixture yielding a BRD9647 deuterated analog. The product was obtained in 96% yield (144 mg, 0.33 mmol) as off-white solid and pure as measured by LCMS and NMR analyses. NMR spectra of were measured using chloroform-d and a frequency of 400 mHz resulting in chemical shifts of δ (ppm)=7.69 (d, J=3.1 Hz, 1H), 7.28 (s, 2H), 7.13 (dd, J=9.0, 3.1 Hz, 1H), 6.95 (d, J=9.1 Hz, 1H), 6.86-6.77 (m, 2H), 3.85 (s, 3H), 3.82 (s, 3H), 3.78 (s, 3H).

Example 3: Activity of Fluoro-Benzoyl Analogs of BRD9647

Figure 1E:
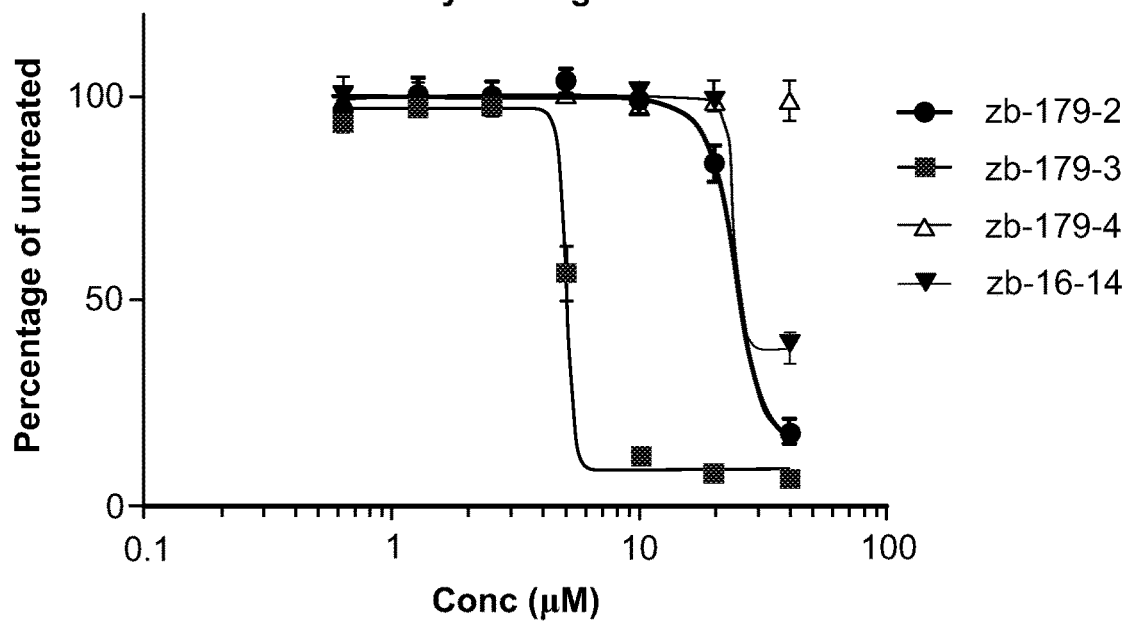
FIGS. 1E-I relates to the dependence of functionalization of the benzoyl group in BRD9647 to MM growth activity.
Figure 1F:
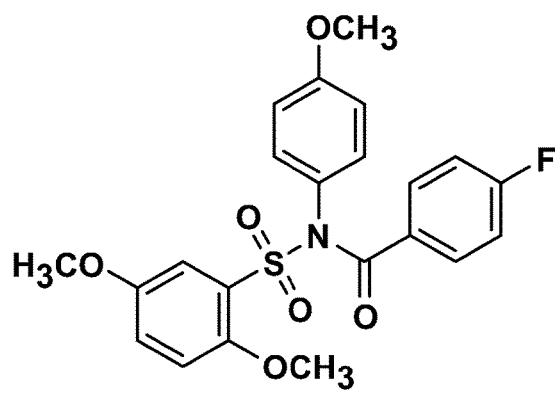
Figure 1G:
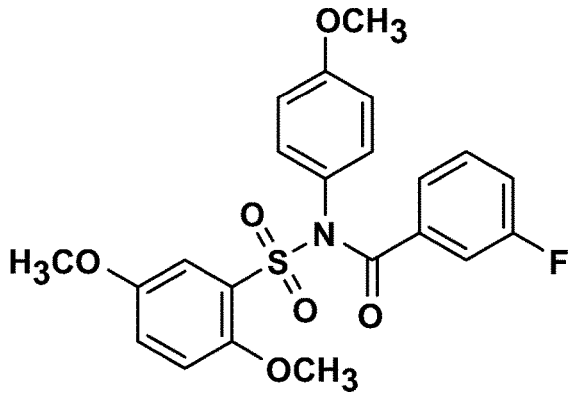
Figure 1H:
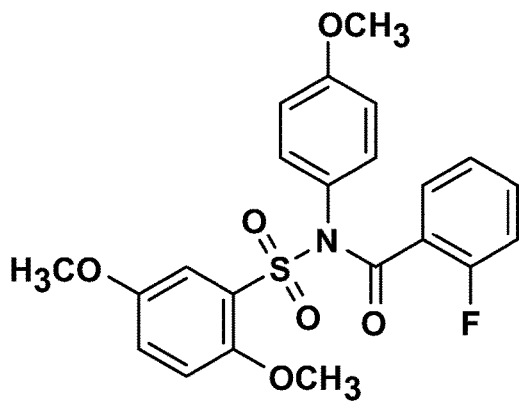
Figure 1I:
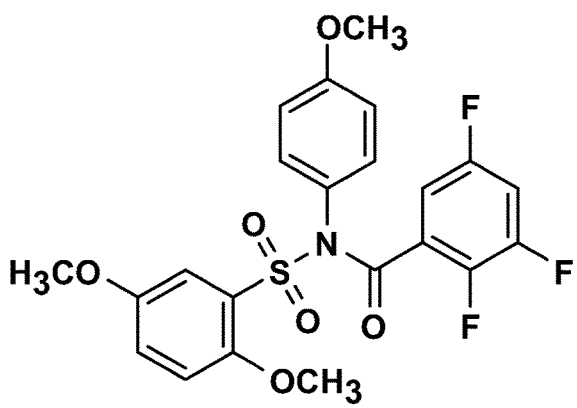

Fluoro-benzoyl analogs of BRD9647 were synthesized and used to study the structure-function relationship between BRD9647 and each compound's ability to inhibit growth in MOLP5 cells. Measurements were performed in a manner similar to the protocol described in Example 1. The BRD9647 analogs measured were either mono-fluorinated at the para (FIG. 1F), meta (FIG. 1G), or ortho (FIG. 1H)

positions of the benzoyl ring, or tri-fluorinated at both meta positions and one ortho position of the ring (FIG. 1I). FIG. 1E shows the viability of MOLP5 treated with various concentrations of these fluoro-benzoyl analogs of BRD9647. As can be seen, the addition of one or more functional groups to the benzoyl rings of BRD9647 alters the MM growth inhibitory activity of each compound. For example, p-fluorobenzyl analogs (e.g., zb-179-3) show increased growth inhibition at each concentration of active over m-fluorobenzoyl (zb-179-2) or o-fluorobenzoyl analogs (zb-16-14). Additionally, all mono substituted analogs appear to inhibit growth substantially more than the tri-fluorinated analog (zb-179-4). Moreover, the p-fluorobenzoyl analog shows similar, if not increased efficacy to BRD9647.

Figure 3:
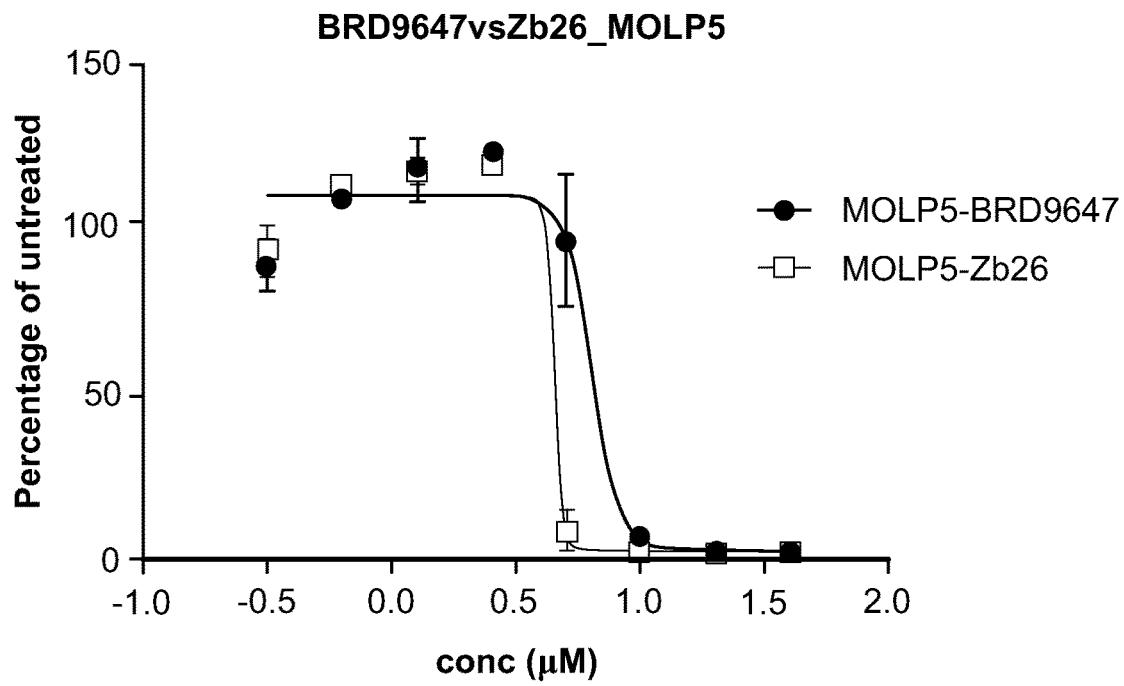
FIG. 3 is a plot showing the viability of MOLP5 treated with various concentrations of an analog of BRD9647 substituted on a phenyl group other than the benzoyl group.

Example 4: Activity of BRD9647 Analogs with Carbon Functionalization Outside the Benzoyl Moiety Compound 5 (i.e., ZB_13_26) was synthesized and used to study the structure-function relationship between BRD9647 and Compound 5's ability to inhibit growth in MOLP5 cells. Measurements were performed in a manner similar to the protocol described in Example 1. FIG. 3 shows the viability of MOLP5 treated with various concentrations of BRD9647 or Compound 5. As can be seen, alteration of the functional groups of BRD9647 produces some changes in the MM growth inhibitory activity the compound. However, alteration of functional groups of the BRD9647 scaffold still provides activity against MOLP5 cell growth. For example, BRD9647 analogs that have replaced the meta-methoxy group on the benzenesulfonyl moiety with a bromine functional group shows similar activity to BRD9647.

Figure 4A:
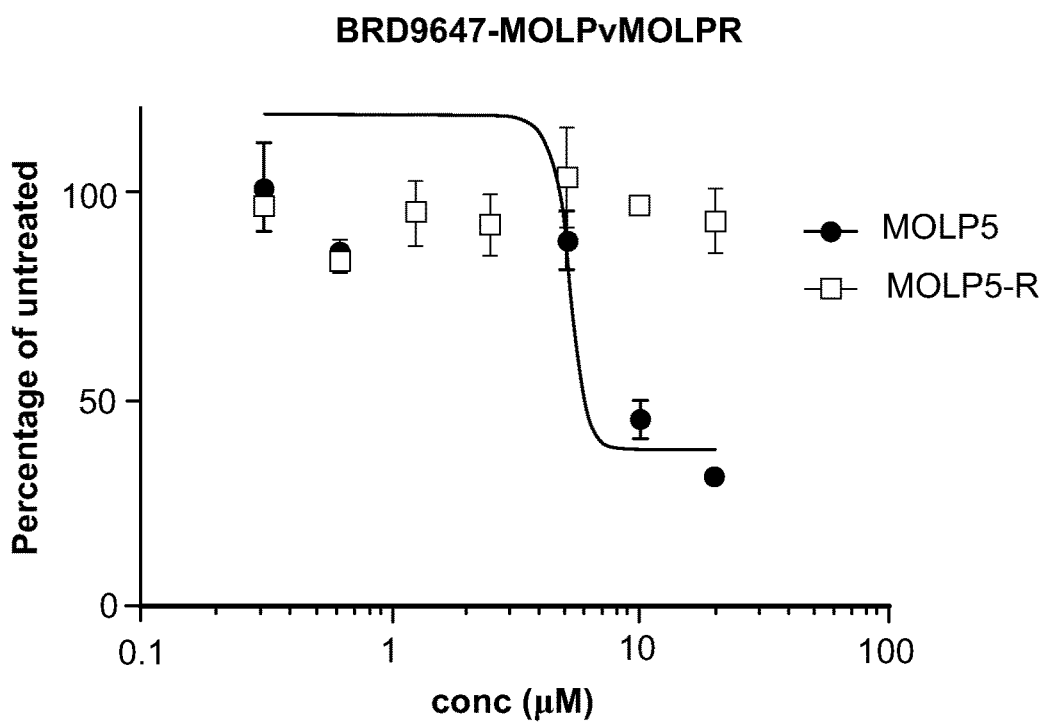
FIGS. 4A-4C are plots showing that MOLP5 cells raised to be resistant to BRD9647 contained a loss of an AZIN1 mutation.
Figure 4B:
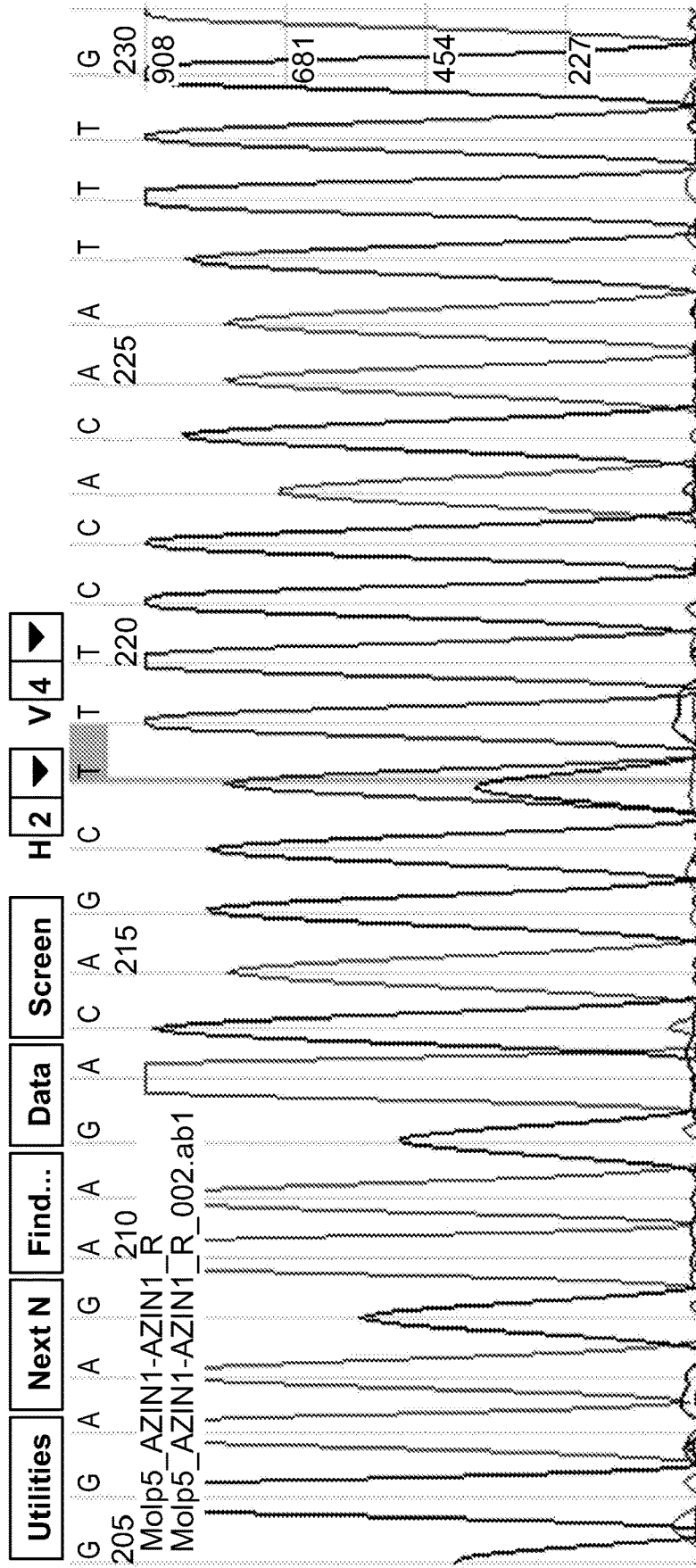
Figure 4C:
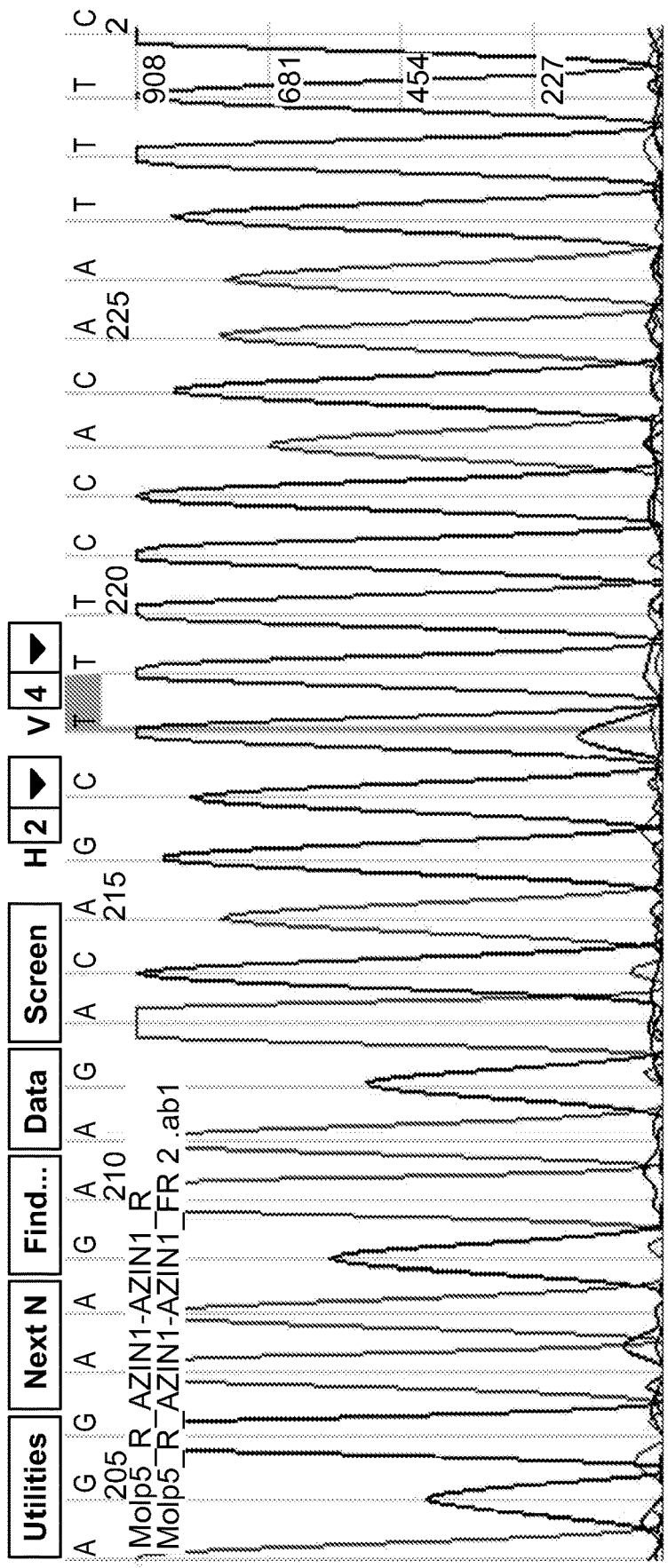
Figure 5A:
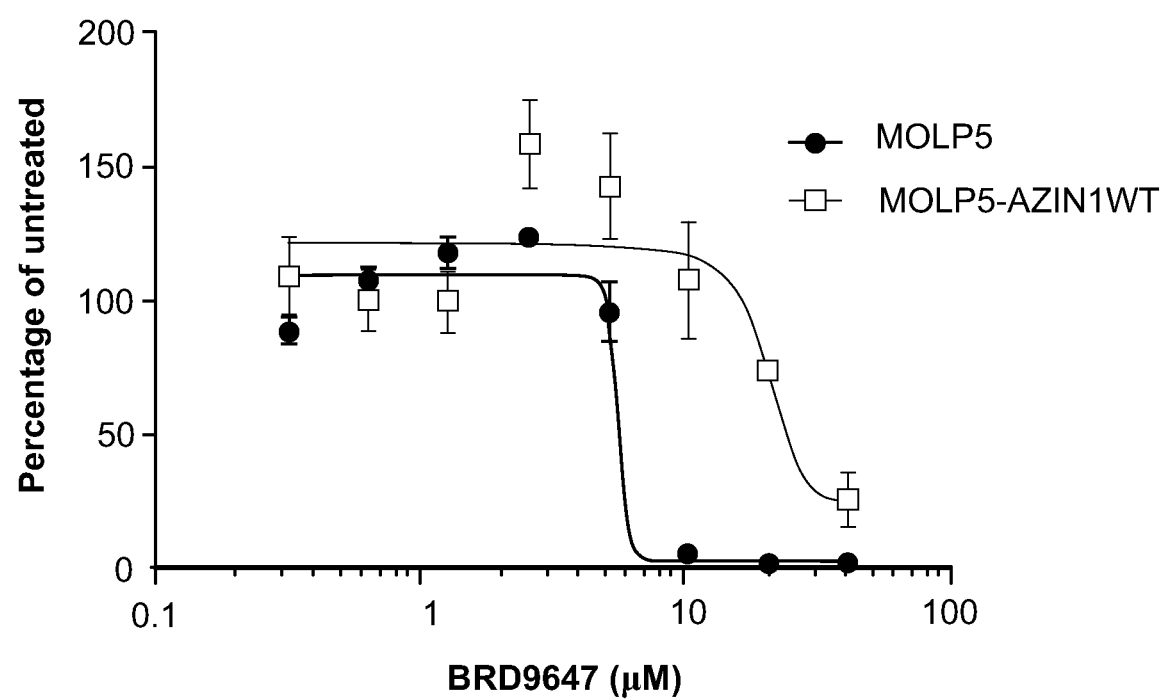
FIGS. 5A-5C are plots showing that wild-type AZIN1 expression in MOLP5 cells conferred resistance to BRD9647.
Figure 5B:
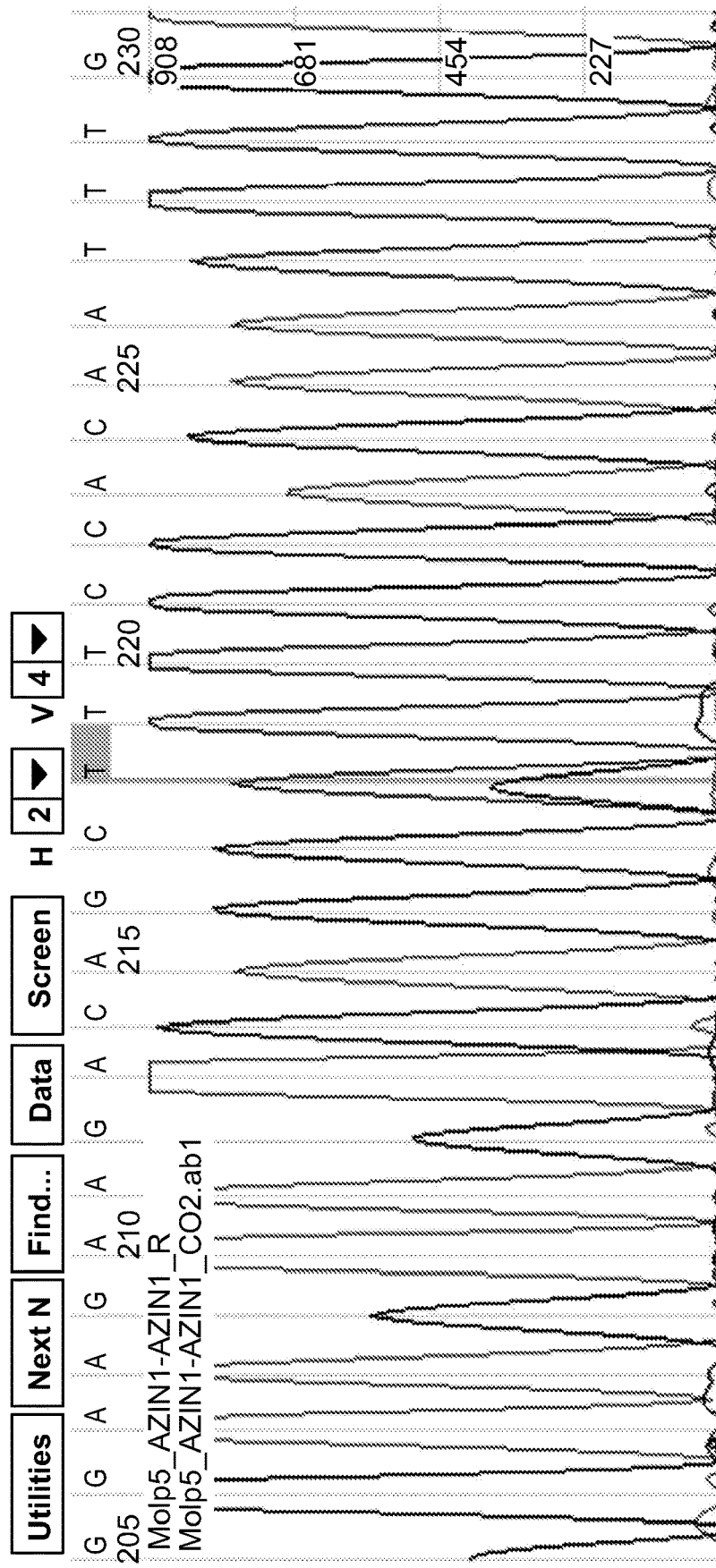
Figure 5C:
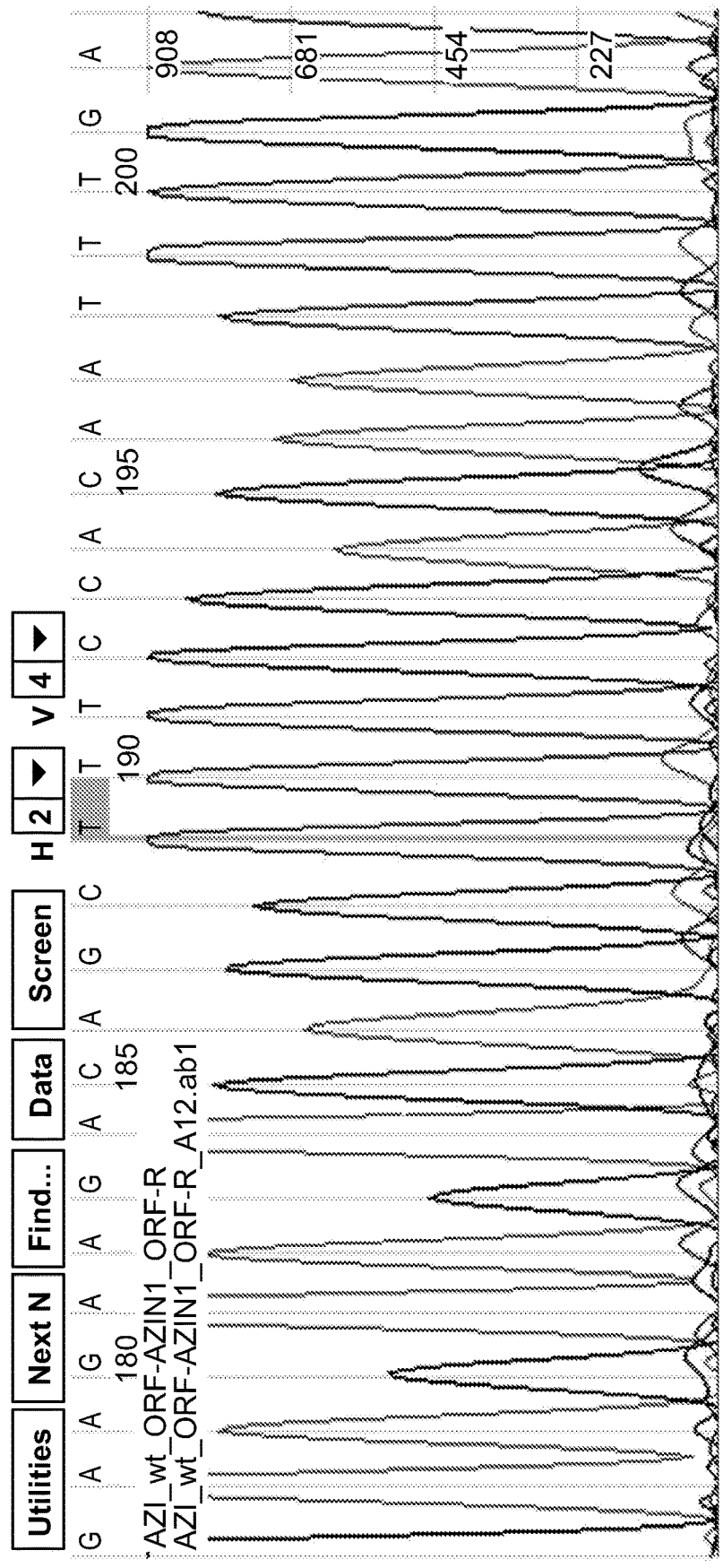
Figure 6:
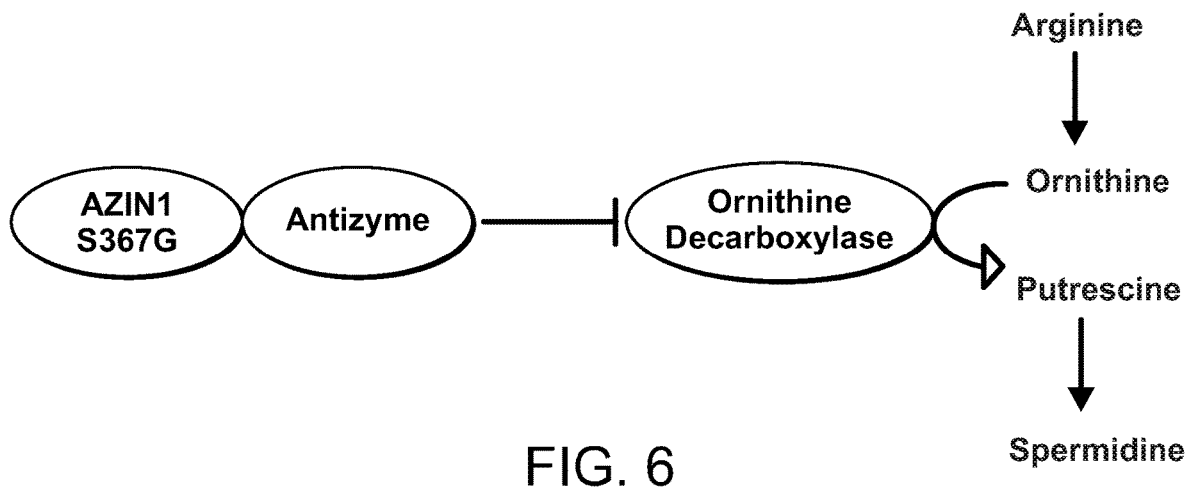
FIG. 6 is a schematic representation showing the effect of AZIN1 in polyamine biosynthesis.

Example 5: Multiple Myeloma Cells Sensitive to BRD9647 Harbored a Mutation in AZIN1, a Gene Involved in Polyamine Biosynthesis Cells selected for resistance to BRD9647 contained alterations in the AZIN1 gene and showed various activities with respect to BRD9647 (FIGS. 4A-4C). MOLP5 cells sensitive to BRD9647 contained a mutation in AZIN1 (FIG. 4B). The mutation in AZIN1 was S367G. MOLP5 cells raised to be resistant to BRD9647 through serial exposures to increasing concentrations of BRD9647 over 3 months (MOLP5-R) lost the AZIN1 mutation that conferred sensitivity to BRD9647 (FIG. 4C). For experiments in FIGS. 4B and 4C, RNA was isolated from MOLP5 or MOLP5-R cells and converted into complementary DNA (cDNA). The AZIN1 polynucleotide was PCR amplified from cDNA then subject to Sanger sequencing. FIG. 4D shows images depicting the viability of MOLP5 cells expressing AZIN1-WT (MOLP5-AzinWT) in contrast to MOLP5 cells expressing the AZIN1-S367G mutation that are sensitive to BRD9647. The growth of MOLP5 AZIN1-WT expressing cells in the presence of BRD9647 resembles the growth of untreated MOLP5 cells. For these experiments, lentiviral vectors (pLX_TRC304) encoding the AZIN1 open reading frame with the wild-type sequence or S367G mutant sequence and the puromycin resistance gene were transduced into MOLP5 cells which were then subjected to puromycin selection. FIGS. 5A-5C show that wild-type AZIN1 expression in MOLP5 cells conferred resistance to BRD9647. A schematic of AZIN1 S367G's role in polyamine synthesis is shown at FIG. 6.

Figure 7A:
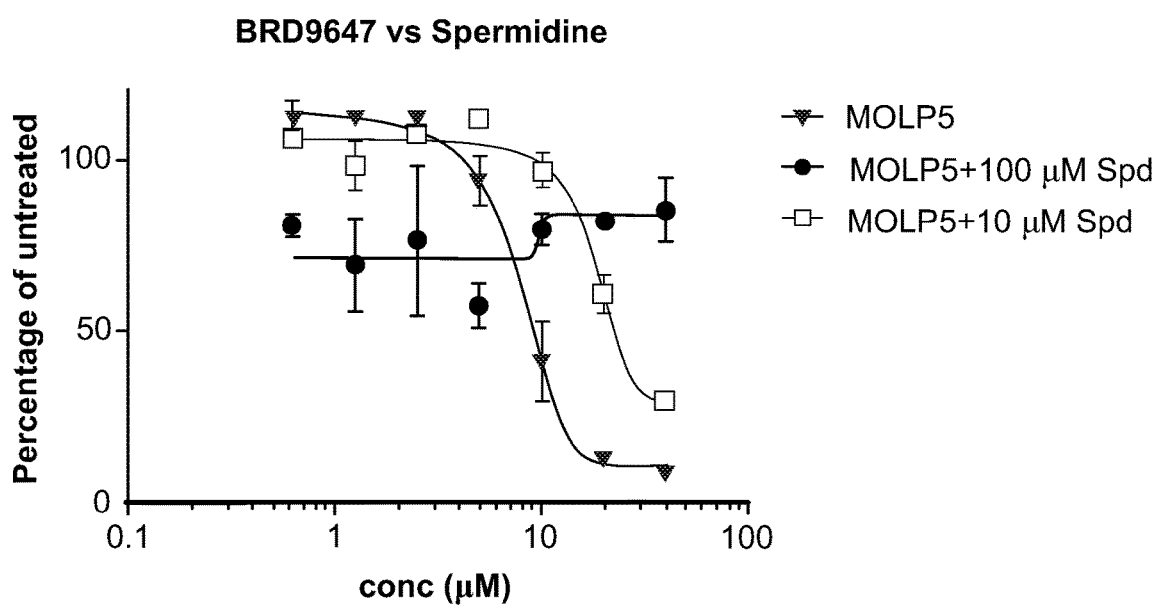
FIGS. 7A-7C show that excess spermidine rescued BRD9647 growth inhibition.
Figure 7B:
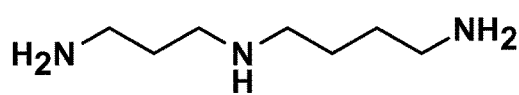
Figure 7C:
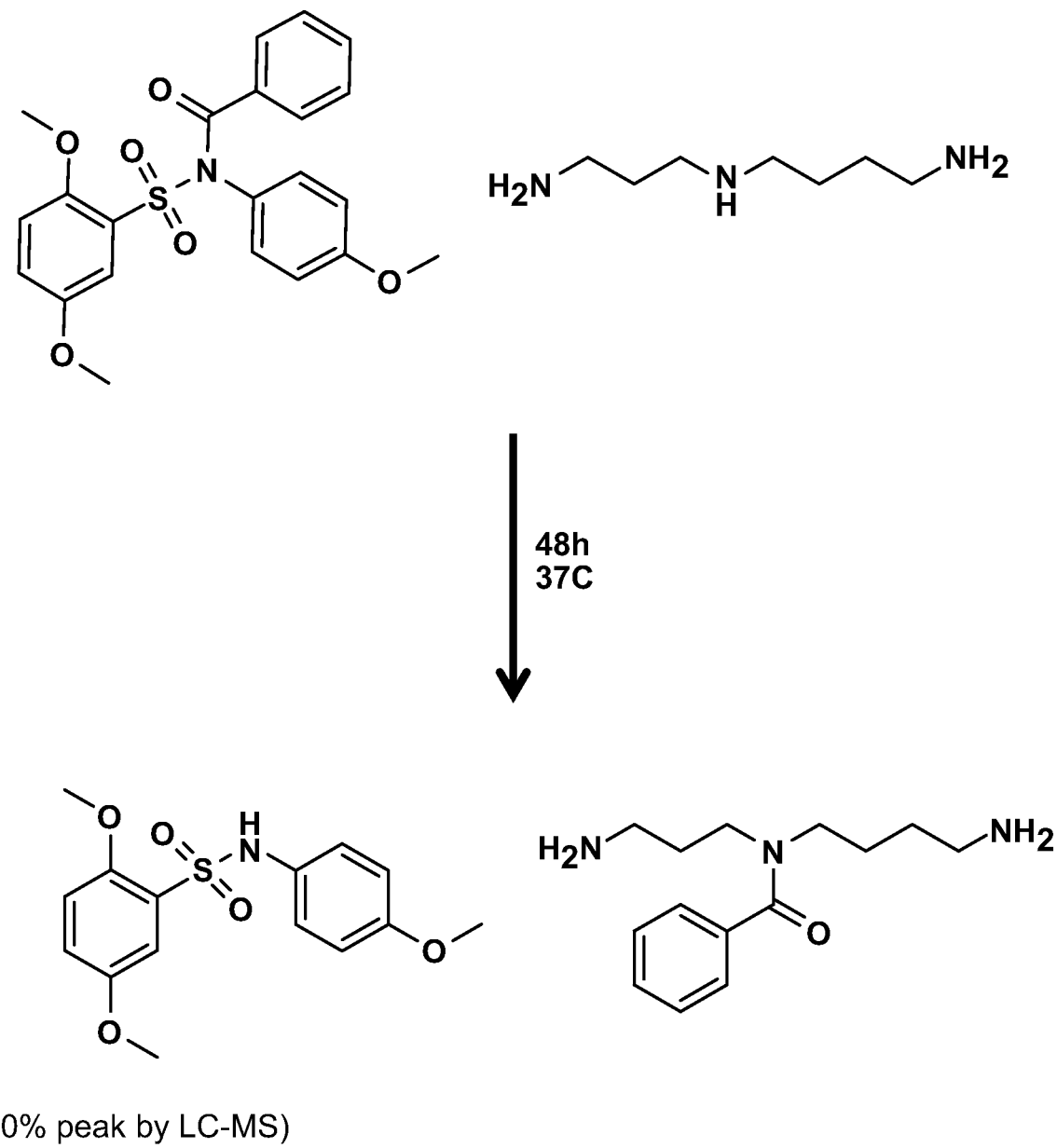
Figure 8:
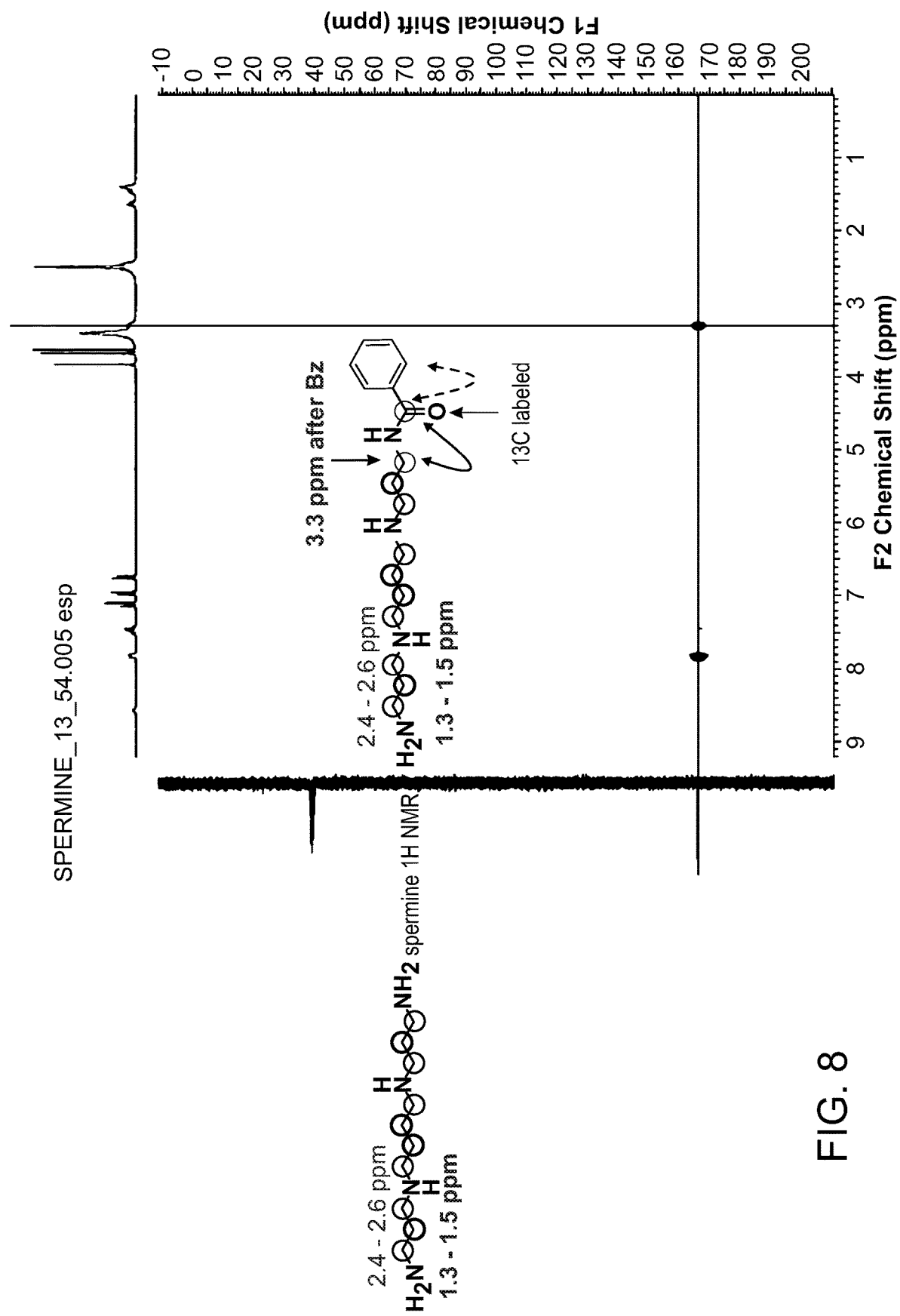
FIG. 8 is a heteronuclear multiple-bond correlation (HMBC) spectroscopy plot showing the structure of an adduct of spermine and BRD9647.
Figure 9:
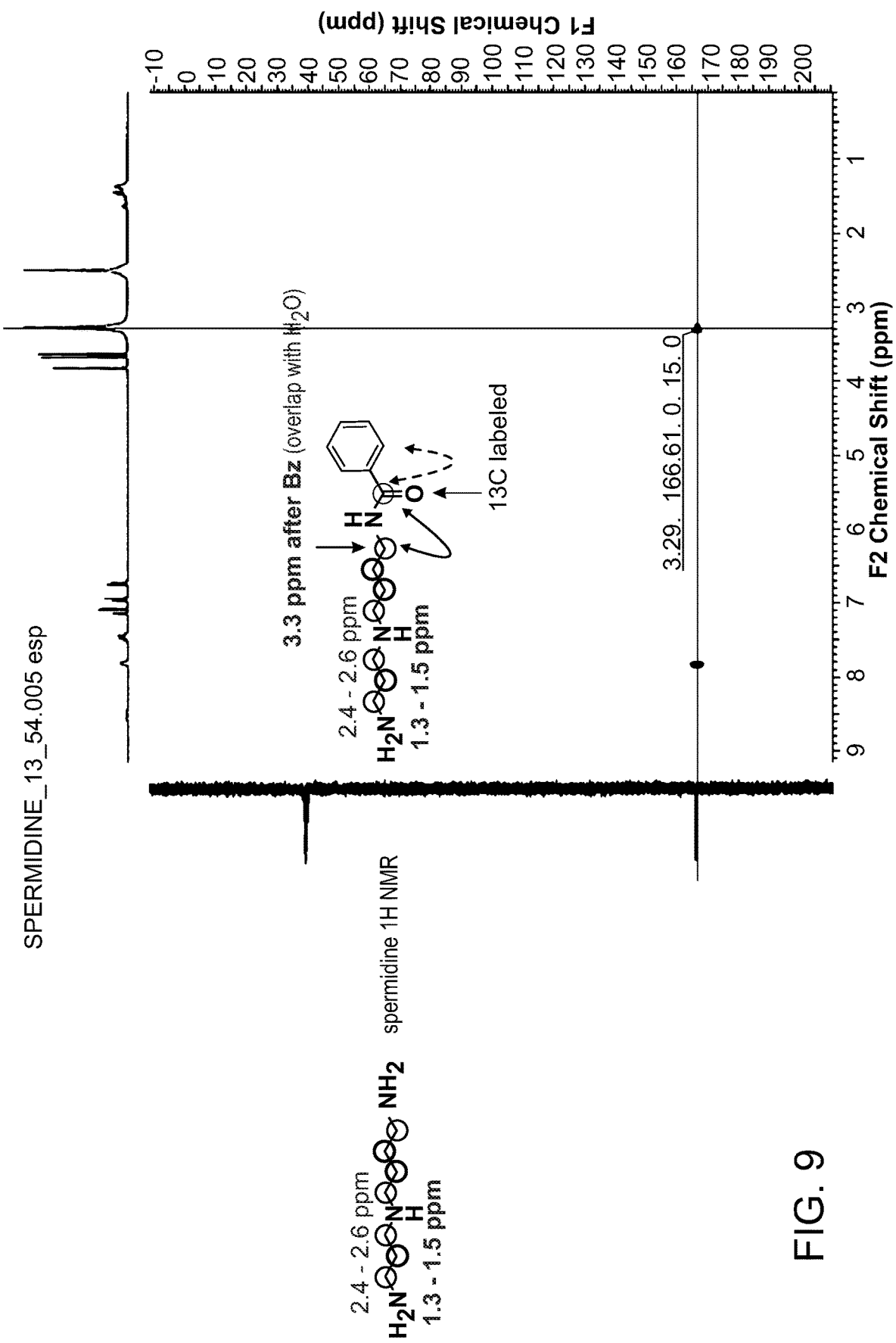
FIG. 9 is a heteronuclear multiple-bond correlation (HMBC) spectroscopy plot showing the structure of an adduct of spermidine and BRD9647.

Polyamines such as spermidine rescued the effects of BRD9647. FIG. 7B depicts the structure of spermidine. FIG. 7A shows that excess spermidine rescued BRD9647 growth inhibition. However, BRD9647 may be reactive with spermidine, as polyamines such as spermidine or spermine can directly react with BRD9647 via a benzoylation reaction (FIG. 7C) to form benzoylated polyamine products (FIG. 8 and FIG. 9).

Figure 10:
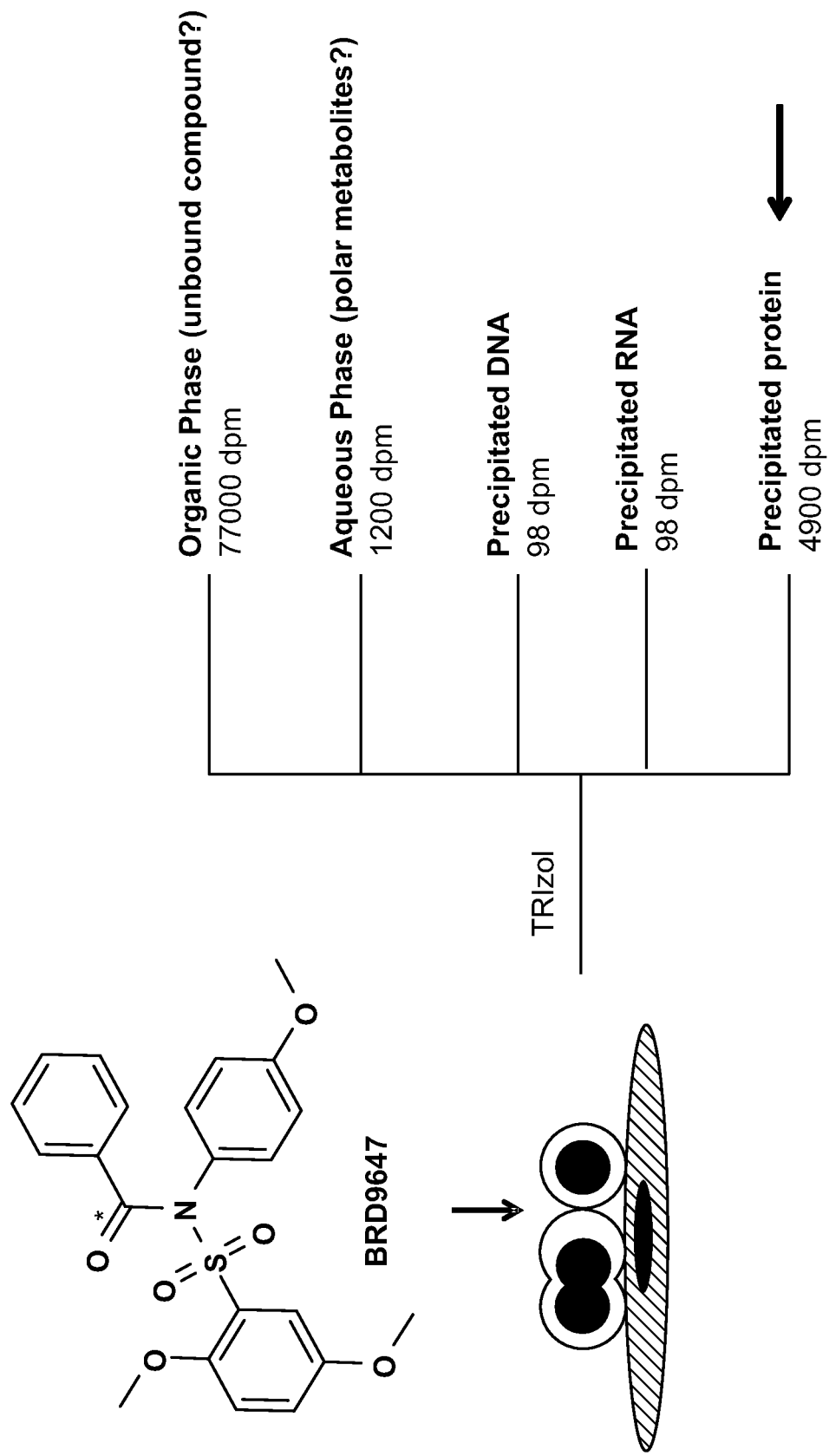
FIG. 10 is a diagram depicting a tracing experiment with a TRIzol treated extract of cells treated with $^{14}$C-BRD9647. Results of the $^{14}$C-BRD9647 tracing experiments suggest protein binding or modification of proteins with $^{14}$C-BRD9647.
Figure 11:
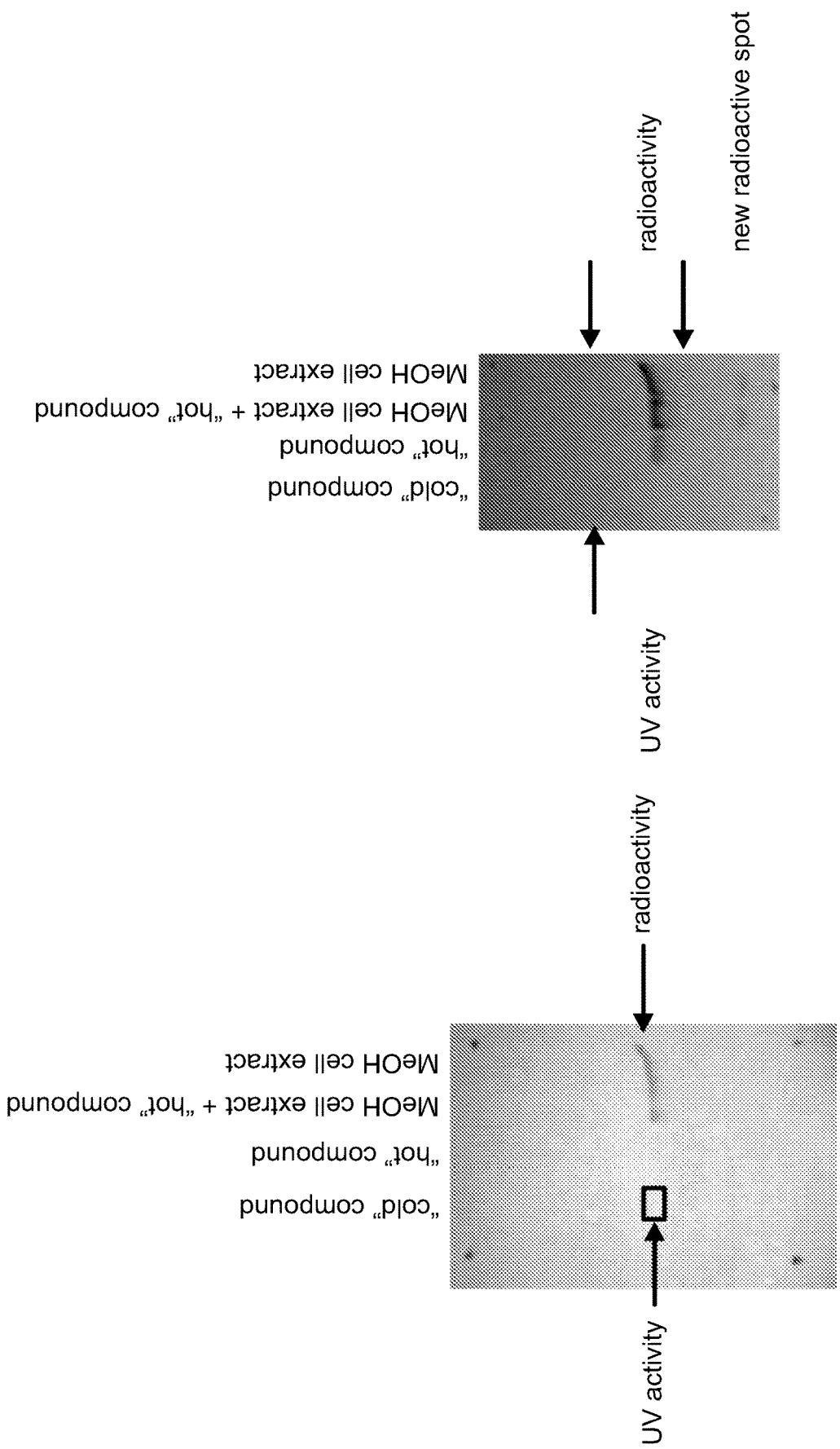
FIG. 11 is a set of thin-layer chromatograms of methanolic cellular extracts of cells treated with radiolabeled BRD9647.

Example 6: Treatment of Cells with Labeled BRD9647 Resulted in Reaction of BRD9647 with Proteins in the Cells Tracing experiments showed that radiolabeled BRD9647 and heavy-isotope labeled BRD9647 reacted with proteins, likely with amine-containing amino acids such as lysines. FIG. 10 is a diagram showing results of a tracing experiment with a TRIzol treated extract of cells treated with 10 µM $^{14}$C-BRD9647 for six hours. Results of the $^{14}$C-BRD9647 tracing experiments suggest protein binding or modification of proteins with $^{14}$C-BRD9647. FIG. 11 shows results of thin-layer chromatography of methanolic cellular extracts of cells treated with radiolabeled BRD9647 for six hours. Some portion of BRD9647 that penetrated the cell appeared to be unmodified, but a new radioactive band appeared in the polar front indicating that BRD9647 was likely metabolite-reactive.

Figure 12:
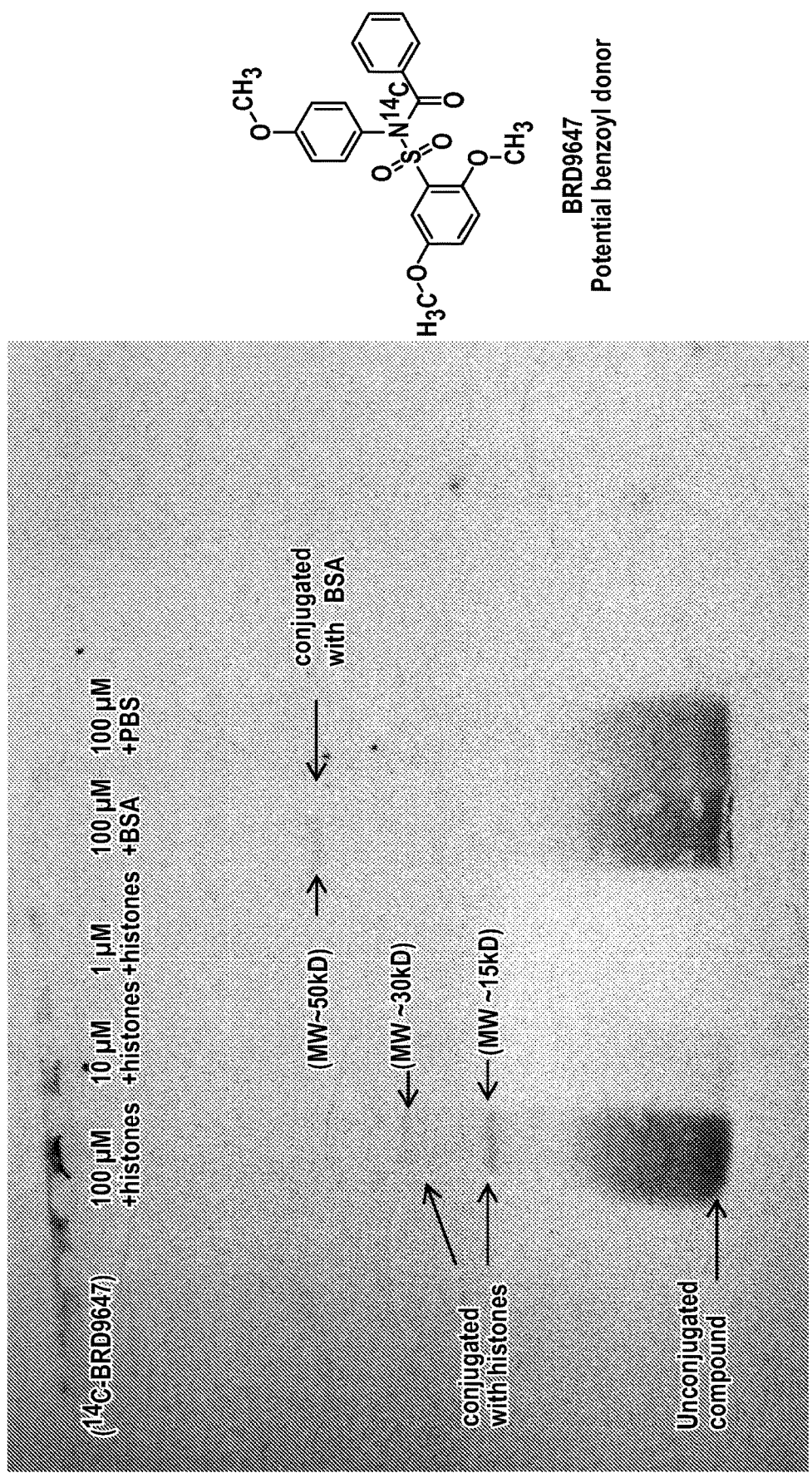
FIG. 12 is a SDS-PAGE autoradiogram showing that covalent binding of $^{14}$C-BRD9647 with purified proteins was possible.
Figure 14:
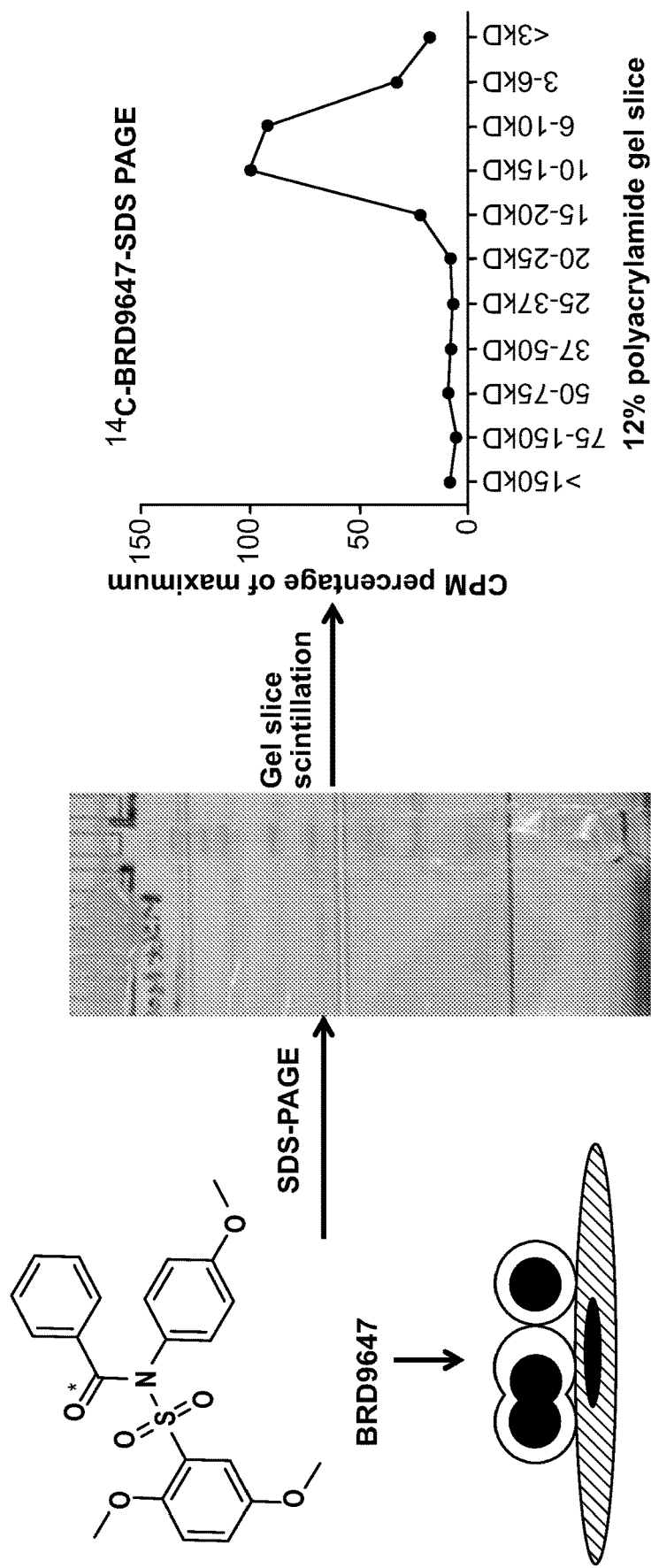
FIG. 14 is a diagram depicting workflow and results of a $^{14}$C-BRD9647 tracing experiment. Results of $^{14}$C-BRD9647 tracing experiments in BRD9647-sensitive cells indicate tight protein binding at ~15 kD molecular weight.

FIG. 12 shows covalent binding of $^{14}$C-BRD9647 with purified proteins was possible. As shown in FIG. 12, discrete, high-molecule weight bands are visible by denaturing SDS-PAGE autoradiography when $^{14}$C-BRD9647 was incubated with recombinant proteins but not PBS buffer. FIG. 13 shows results of mass spectrometry of $^{13}$C-BRD9647 co-incubated with histones, which identify labeled lysines. In FIG. 14, the workflow and results of a $^{14}$C-BRD9647 tracing experiment with protein extract from cells treated with $^{14}$C-BRD9647 are shown. Results of $^{14}$C-BRD9647 tracing experiments in BRD9647-sensitive cells indicate tight protein binding at ~15 kD molecular weight. FIG. 15 shows results of immunoblotting to detect benzoylated lysines on proteins using an antibody directed against benzoylated lysines (Kbz). In samples obtained from cells treated with BRD9647 an increase in benzoylated lysines were detected in contrast to controls treated with DSMO by Western blotting with images acquired by short and long time exposures (FIG. 14, left panel).

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A compound having the structure of Formula (I):

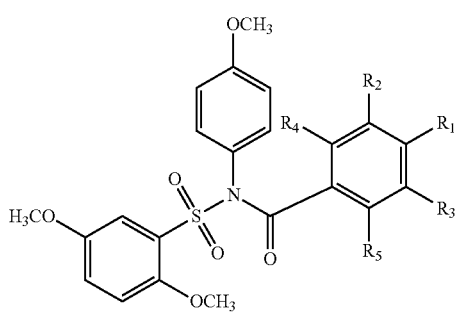

(I)

wherein $R_1$-$R_5$ are independently selected from hydrogen, —F; —Cl; —Br; —I; —OH; —OR*; —NH$_2$; —NHR*; —N(R*)$_2$; —N(R*)$_3^+$; —N(R*)—OH; —N(→*O)(R*)$_2$; —O—N(R*)$_2$; —N(R*)—O—R*; —N(R*)—N(R*)$_2$; —C=N—R*; —N=C(R*)$_2$; —C=N—N(R*)$_2$; —C(=NR*)(—N(R*)$_2$); —C(H)(=N—OH); —SH; —SR*; —CN; —NC; —C(=O)—R*; —CHO; —CO$_2$H; —CO$_2$—; —CO$_2$R*; —C(=O)—S—R*; —O—(C=O)—H; —O—(C=O)—R*; —S—C(=O)—R*; —(C=O)—NH$_2$; —C(=O)—N(R*)$_2$; —C(=O)—NHNH$_2$; —O—C(=O)—NHNH$_2$; —C(=S)—NH$_2$; —(C=S)—N(R*)$_2$; —N(R*)—CHO; —N(R*)—C(=O)—R*; —C(=NR*)—O—R*; —O—C(=NR*)—R*; —SCN; —NCS; —NSO; —SSR*; —N(R*)—C(=O)—N(R*)$_2$; —N(R*)—C(=S)—N(R*)$_2$; —S(=O)$_{1-2}$—R*; —O—S(=O)$_2$—R*; —S(=O)$_2$—OR*; —N(R*)—S(=O)$_2$—R*; —S(=O)$_2$—N(R*)$_2$; —O—SO$_3$; —O—S(=O)$_2$—OR*; —O—S(=O)—OR*; —O—S(=O)—R*; —S(=O)—OR*; —S(=O)—R*; —NO; —NO$_2$; —NO$_3$; —O—NO; —O—NO$_2$; —N$_3$; —N$_2$—R*; —N(C$_2$H$_4$); —Si(R*)$_3$; —CF$_3$; —O—CF$_3$; —O—CH$_3$; —O—(CH$_2$)$_{1-6}$CH$_3$; —PR*$_2$; —O—P(=O)(OR*)$_2$; and —P(=O)(OR*)$_2$;

$R^*$ is, independently at each occurrence from hydrogen, and a $C_{1-10}$ hydrocarbon; where at least one of $R_1$-$R_5$ is not hydrogen;

or pharmaceutically acceptable salts thereof.

2. The compound according to claim 1, wherein $R_1$ is fluorine, chlorine, bromine, or iodine and wherein $R_2$-$R_5$ are each hydrogen.

3. The compound according to claim 1, wherein $R_2$, $R_3$, $R_4$ and/or $R_5$ are independently fluorine, chlorine, bromine or iodine.

4. The compound according to claim 1 where in $R_1$-$R_5$ are independently selected from the group consisting of hydrogen, —OH, —SH, —NH$_2$; —N(R*)$_2$; —OR*; —F; —Cl; and —Br.

5. A compound having the structure:

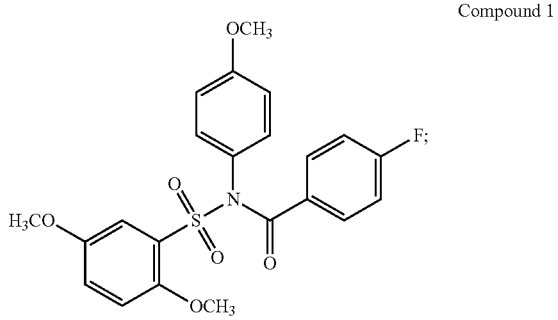

Compound 1

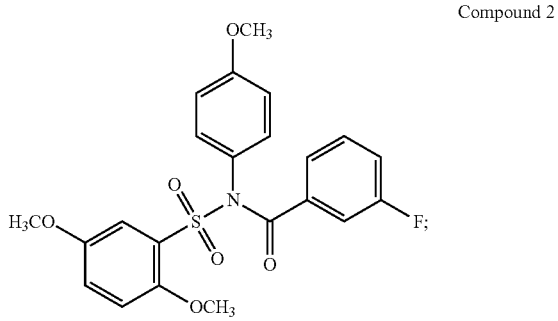

Compound 2

Compound 3
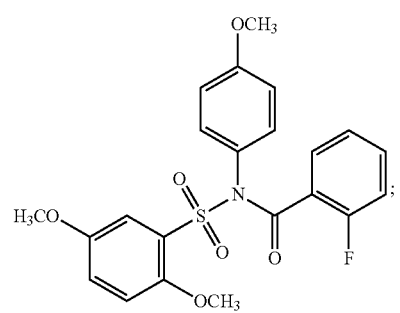
Compound 4
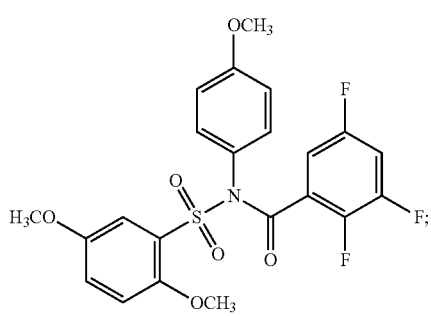
Compound 5
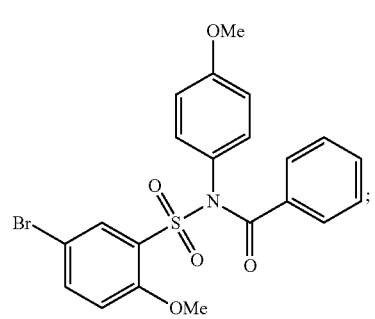
Compound 6
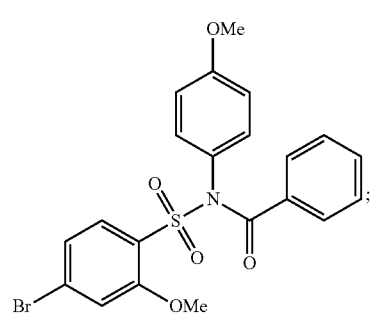
Compound 7
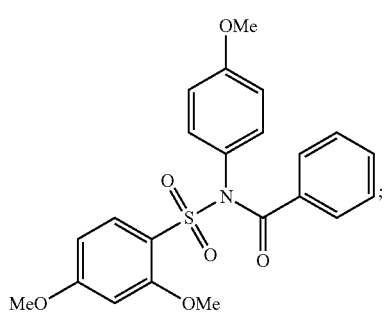
Compound 8
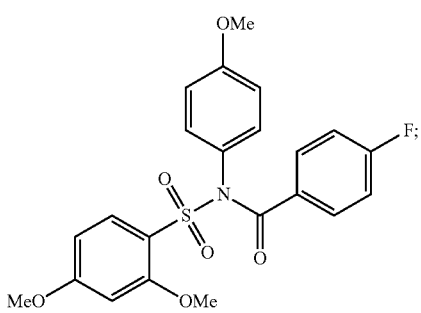
Compound 9
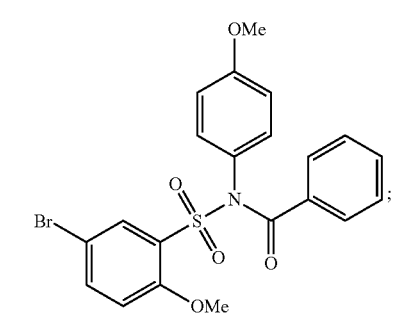
Compound 11
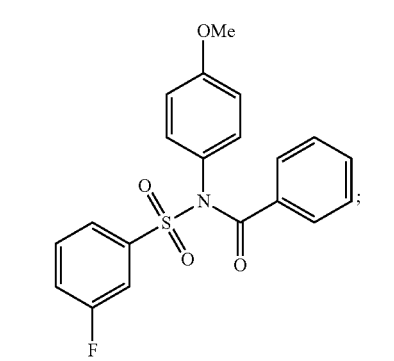
Compound 12
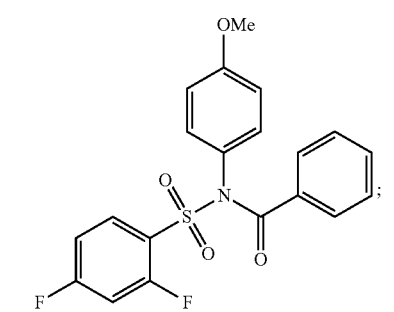

Compound 13

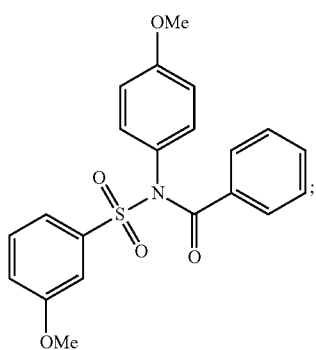

Compound 14

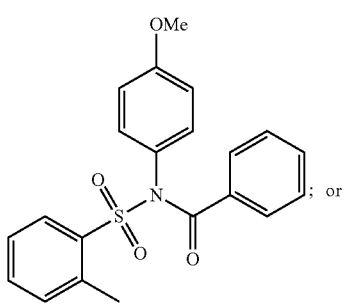

; or

Compound 15

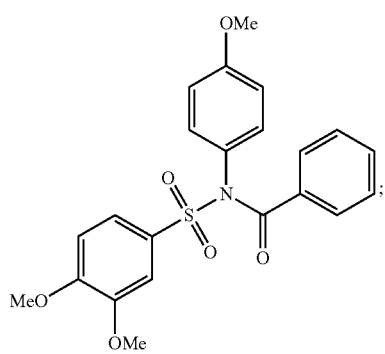

;

and pharmaceutically acceptable salts thereof.

6. A method of inhibiting proliferation of a multiple myeloma cell, the method comprising contacting the cell with BRD9647 having the following structure:

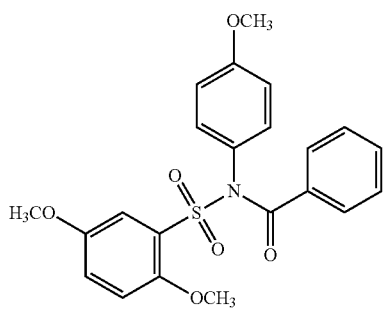

thereby inhibiting proliferation of the cell.

7. A pharmaceutical composition comprising an effective amount of BRD9647 having the following structure:

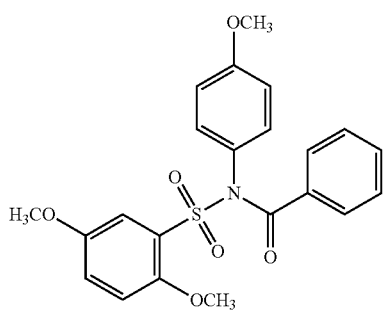 [SMILES: COc1ccc(N(C(=O)c2ccccc2)S(=O)(=O)c2cc(OC)ccc2OC)cc1]

in a pharmaceutically acceptable carrier.

8. A method of treating multiple myeloma in a subject, the method comprising administering to the subject the pharmaceutical composition of claim 7.

9. A kit comprising the pharmaceutical composition of claim 7.

10. A pharmaceutical composition comprising an effective amount of a compound of claim 1 in a pharmaceutically acceptable carrier.

11. A kit comprising the pharmaceutical composition of claim 10.

12. A method of treating multiple myeloma in a subject, the method comprising administering to the subject a compound of claim 1.

13. A method of inhibiting proliferation of a multiple myeloma cell, the method comprising contacting the cell with a compound of claim 1, thereby inhibiting proliferation of the cell.

\* \* \* \* \*

SEQUENCE LISTING

<160> NUMBER OF SEQ ID NOS: 10

<210> SEQ ID NO 1
<211> LENGTH: 448
<212> TYPE: PRT
<213> ORGANISM: Homo sapiens

<400> SEQUENCE: 1

```
Met Lys Gly Phe Ile Asp Asp Ala Asn Tyr Ser Val Gly Leu Leu Asp
1               5                   10                  15

Glu Gly Thr Asn Leu Gly Asn Val Ile Asp Asn Tyr Val Tyr Glu His
            20                  25                  30

Thr Leu Thr Gly Lys Asn Ala Phe Phe Val Gly Asp Leu Gly Lys Ile
        35                  40                  45

Val Lys Lys His Ser Gln Trp Gln Asn Val Val Ala Gln Ile Lys Pro
50                  55                  60

Phe Tyr Thr Val Lys Cys Asn Ser Ala Pro Ala Val Leu Glu Ile Leu
65                  70                  75                  80

Ala Ala Leu Gly Thr Gly Phe Ala Cys Ser Ser Lys Asn Glu Met Ala
                85                  90                  95

Leu Val Gln Glu Leu Gly Val Pro Pro Glu Asn Ile Ile Tyr Ile Ser
            100                 105                 110

Pro Cys Lys Gln Val Ser Gln Ile Lys Tyr Ala Ala Lys Val Gly Val
        115                 120                 125

Asn Ile Leu Thr Cys Asp Asn Glu Ile Glu Leu Lys Lys Ile Ala Arg
130                 135                 140

Asn His Pro Asn Ala Lys Val Leu Leu His Ile Ala Thr Glu Asp Asn
145                 150                 155                 160

Ile Gly Gly Glu Glu Gly Asn Met Lys Phe Gly Thr Thr Leu Lys Asn
                165                 170                 175

Cys Arg His Leu Leu Glu Cys Ala Lys Glu Leu Asp Val Gln Ile Ile
            180                 185                 190

Gly Val Lys Phe His Val Ser Ser Ala Cys Lys Glu Ser Gln Val Tyr
        195                 200                 205

Val His Ala Leu Ser Asp Ala Arg Cys Val Phe Asp Met Ala Gly Glu
210                 215                 220

Ile Gly Phe Thr Met Asn Met Leu Asp Ile Gly Gly Gly Phe Thr Gly
225                 230                 235                 240

Thr Glu Phe Gln Leu Glu Glu Val Asn His Val Ile Ser Pro Leu Leu
                245                 250                 255

Asp Ile Tyr Phe Pro Glu Gly Ser Gly Val Lys Ile Ile Ser Glu Pro
            260                 265                 270

Gly Ser Tyr Tyr Val Ser Ser Ala Phe Thr Leu Ala Val Asn Ile Ile
        275                 280                 285

Ala Lys Lys Val Val Glu Asn Asp Lys Phe Pro Ser Gly Val Glu Lys
            290                 295                 300

Thr Gly Ser Asp Glu Pro Ala Phe Met Tyr Tyr Met Asn Asp Gly Val
305                 310                 315                 320

Tyr Gly Ser Phe Ala Ser Lys Leu Ser Glu Asp Leu Asn Thr Ile Pro
                325                 330                 335

Glu Val His Lys Lys Tyr Lys Glu Asp Glu Pro Leu Phe Thr Ser Ser
            340                 345                 350

Leu Trp Gly Pro Ser Cys Asp Glu Leu Asp Gln Ile Val Glu Ser Cys
        355                 360                 365
```

```
Leu Leu Pro Glu Leu Asn Val Gly Asp Trp Leu Ile Phe Asp Asn Met
370                 375                 380

Gly Ala Asp Ser Phe His Glu Pro Ser Ala Phe Asn Asp Phe Gln Arg
385                 390                 395                 400

Pro Ala Ile Tyr Tyr Met Met Ser Phe Ser Asp Trp Tyr Glu Met Gln
                405                 410                 415

Asp Ala Gly Ile Thr Ser Asp Ser Met Met Lys Asn Phe Phe Phe Val
                420                 425                 430

Pro Ser Cys Ile Gln Leu Ser Gln Glu Asp Ser Phe Ser Ala Glu Ala
            435                 440                 445
```

<210> SEQ ID NO 2
<211> LENGTH: 4239
<212> TYPE: DNA
<213> ORGANISM: Homo sapiens

<400> SEQUENCE: 2

```
ctaatataaa tactggcgtc gctggcgccg ccttctcaca ctttcaggct ctgatcgcgg      60
ccgcagtttt tccttttttc ttctgccgtc gccttctctg cctcttctca tcctttctcg     120
ctctgctgct ctgcagtgtg acgagtccga atcctcttcc cacccagccc gcgccttcct     180
tcttttgcct gcgctgttct atttctcctt cggccgccgc cgccactgct gcacacagct     240
ggtgtcggtg ccgcgctttt accccaagt cgttcccgca gcctatggcc caggccgcct     300
tgggtatttc tgctcaaggt aaccacatcc ctctttaaaa attccgccga aaagagaag      360
acgctttacc cgactctttg ggccgttatc tcacggcgaa ctttctgacc aagtatacaa     420
ctacccagag ggcctaggag aagtgctgta tagagagcag ttcgacttca acgctgagcc     480
accttgggaa cctagctgat gataggggg ttccatctcc caacttgtcc attttgttgc      540
atattctaag gacccagaca taggcttggt ggcccgtctc ttgtctttcc tggtttatga     600
cttctggctt tgtggaatac ggctgagatg aaaggattta ttgatgatgc aaactactcc     660
gttggcctgt tggatgaagg aacaaacctt ggaaatgtta ttgataacta tgtttatgaa     720
catacccctga cagggaaaaa tgcattttttt gtgggagatc ttggaaagat tgtgaagaaa     780
cacagtcaat ggcagaatgt agtggctcag ataaagccat tctacacagt gaagtgcaac     840
tctgctccag ctgtacttga tttttggca gctcttggaa ccggatttgc ttgttccagt      900
aaaaatgaaa tggctttagt gcaagagttg ggtgtacctc agaaaacat tatttacata      960
agtccttgca gcaagtgtc tcagataaag tatgcagcaa agttggagt gaatatcctg      1020
acatgtgaca atgaaattga attgaagaaa attgcacgta atcacccaaa tgccaaggtc     1080
ttactacata ttgcaacaga agataatatt ggaggtgaag agggtaacat gaagtttggc     1140
actaccctga gaactgtag gcatctcttg gaatgtgcta aggaacttga tgtccaaata     1200
attggggtta aatttcatgt ttcgagtgct tgcaaagaat ctcaagtata tgtacatgct     1260
ctatctgatg ctcgatgtgt gtttgacatg gctgagaaa ttggctttac gatgaacatg     1320
ttagacattg gtgaggatt cacgggaact gaatttcaat tggaagaggt taatcatgtt     1380
atcagccctc tgttggatat ctactttcct gaaggatctg tgttaagat aatttcagaa     1440
cccgaagct actatgtgtc ttctgcattt acactcgcag ttaatatcat agcaaagaaa     1500
gttgttgaaa atgataaatt tccctctgga gtagaaaaaa ccggaagtga tgaaccagcc     1560
ttcatgtatt atatgaatga tggtgtttat ggttcttttg caagtaaact gtctgaggac     1620
ttaaatacca ttccagaggt tcacaagaaa tacaaggaag atgagcctct gtttacaagc     1680
```

```
agcctttggg gtccatcctg tgatgagctt gatcaaattg tggaaagctg tcttcttcct    1740
gagctgaatg tgggagattg gcttatcttt gataacatgg gagcagattc tttccatgaa    1800
ccatctgctt ttaatgattt tcagaggcca gccatttatt acatgatgtc attcagtgat    1860
tggtatgaga tgcaagatgc tggaattact tcagactcaa tgatgaagaa cttcttcttt    1920
gtgccttctt gcattcagct gagccaagaa dacagctttt ccgctgaagc ttaaacaggc    1980
attaacgctt ctttagatct gaagttgcag gttaagcttg tctggtcaac attccagtgt    2040
ggaaaaataa tttaaacaat cttattctct taattctttt ggcaacaaaa actattagta    2100
atagctattt gggaccagac aaaatcagct ttcatctata attcattggg gataatggga    2160
gatttagata atgtatccag atttaaacct accagtttgt cctacccctt aagcgtttaa    2220
aataaaatat gcaacaaaat ggatgactta gtggagatgg aagcccatta attgggttcc    2280
ccattaaatc gtttacatac aagaacacag ttttttatact aaggatttgt gtttaaagtc    2340
ttgtaaagtt catgtctttc acccagatat atcaaatgtt agaagaccag tgtgacttca    2400
ttagataacg tttagtgtat ttagaatgtg taaatttgtg ctttgaactg tagtttaata    2460
aatgtaaaat tgcatcatag tatttgttga cctaatgtaa cccttgtatg attgcaataa    2520
aattttgtgt agatttact gttttttcag gctaaaactt tgggaaaggg gctagctagc    2580
aaaggtagtt ttgaaataga gtgtatatg gactgttttg aagggttttt ttctttatag    2640
cccagttaag ttttgtttgg ctcggtgcat ttttcattta tttaattagt aatttaagta    2700
aagtgtttgg taaatcattg tgaagttcag attcattatg gagagttgat gtgcagtaag    2760
catgatgttt aacaatttta acaccaaaaa tgttaatcct gcataaatca actgtaataa    2820
taaataggtg tttctgtata gatagaatgc atagagtacc ttagtaaatc tttgaatcac    2880
aatcttttgg ctgaaatgga agattctgtt aaatactttg aataaacttg ggggagggaa    2940
aataaaattg cagaaaactg cagagcacta aaacttaaag aagggctaca tctttatcca    3000
gaaacctgtt gctcttttgc acggaatgtt taaattcaga gttgggatgg ggggtggggt    3060
gaagcacact tattatcttc agttgcagtg atttcaaatt taggattttt tgttgttggt    3120
ttgaactgtc cccttagttt cttgttattt ccaatttgtt ctgcttagtc attacttttta    3180 attcttttct tactaaaatt ttatggtggt tgggggaagg gagttagcat cactaacctg    3240
acagttgttg ccaggaattt gctttgttta ctgctagtat attagaaatc ctagatctca    3300
gaatcacaat agtaataaac aacagggtc attttttcct aacttactct gtgttcaggt    3360
gtggaatttc tgtctcccaa gaggaaatgt gacttcactt tggtgccaat ggacagaaaa    3420
ttctacctgt gctacatagg agaagtttgg aatgcactta atagctggtt tttacacctt    3480
gatttcgagg tggaaagaaa ttgatcatga atctctaata aatttaaatc tcttaaacca    3540
gtaggtgctt aatatttttt gatttgatta atgcccattt aaatctcatg ggttctatta    3600
aaaatatata tatatagggc cccaatccat tgccatcaaa ttgcccttgg acttttccaa    3660
ggtatattat ggggttttat gcaaaattcc aagctaccat gtaactttt ttaaccattt    3720 aacaaggagg gggaactgtt tcctaccttc tttacatgtt gtgcattgtt gtggtccaga    3780
aatgccaaac cttttttaaag atggtgcaac tttgagtcct tggcttgact atacaggcct    3840
tgaacttcat ggcatatcaa ctttgccata tctgcaggag agctgttcta taagaaatag    3900
ctcagagttg caaatatcac atgtgaatga tacggtaact tttaagaaat gtctgtattg    3960
tatttgaaga ctgtttgcca taaatctgaa atttgaacct atgtatttca atttggtatg    4020
ctaaaaagtt ctgaattaat gtaaagtttt ttgttataat attgtaatct cagttcaaaa    4080
```

```
gttaactgca aatataaaac ccaatgattt ctatatagta aattgaactg taaaggtaac    4140
ttgtgtgtga ttctgaatac atagataaat gtttttattc ctcatgtttt actttggctt    4200
ctatctgaaa tagaggtaaa attttacata tcagcttta                           4239
```

```
<210> SEQ ID NO 3
<211> LENGTH: 15
<212> TYPE: PRT
<213> ORGANISM: Homo sapiens

<400> SEQUENCE: 3

Arg Ile Ser Gly Leu Ile Tyr Glu Glu Thr Arg Gly Val Leu Lys
1               5                   10                  15

<210> SEQ ID NO 4
<211> LENGTH: 11
<212> TYPE: PRT
<213> ORGANISM: Homo sapiens

<400> SEQUENCE: 4

Arg Gln Gly Arg Thr Leu Tyr Gly Phe Gly Gly
1               5                   10

<210> SEQ ID NO 5
<211> LENGTH: 12
<212> TYPE: PRT
<213> ORGANISM: Homo sapiens

<400> SEQUENCE: 5

Thr Val Thr Ala Met Asp Val Val Tyr Ala Leu Lys
1               5                   10

<210> SEQ ID NO 6
<211> LENGTH: 18
<212> TYPE: PRT
<213> ORGANISM: Homo sapiens

<400> SEQUENCE: 6

Val Phe Leu Glu Asn Val Ile Arg Asp Ala Val Thr Tyr Thr Glu His
1               5                   10                  15

Ala Lys

<210> SEQ ID NO 7
<211> LENGTH: 11
<212> TYPE: PRT
<213> ORGANISM: Homo sapiens

<400> SEQUENCE: 7

Val Leu Arg Asp Asn Ile Gln Gly Ile Thr Lys
1               5                   10

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggaagaagac agctttccac aatttg                                         26

<210> SEQ ID NO 9
```

```
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aggaagaaga cagctttcca caattt                                          26

<210> SEQ ID NO 10
<211> LENGTH: 26
<212> TYPE: DNA
<213> ORGANISM: Homo sapiens

<400> SEQUENCE: 10
gaagaagaca gctttccaca atttga                                          26
```